(12) United States Patent
Berlowitz et al.

(10) Patent No.: US 9,919,075 B2
(45) Date of Patent: Mar. 20, 2018

(54) COHESIVE MATERIALS INCLUDING DERIVATIZED COLLAGENS AND METHODS OF MAKING AND USING THEM

(71) Applicants: Laurence J Berlowitz, Beverly, MA (US); Hans P. I. Claesson, Lexington, MA (US); Matthew Fullana, Wilmington, MA (US); Gary E Wnek, Cleveland, OH (US)

(72) Inventors: Laurence J Berlowitz, Beverly, MA (US); Hans P. I. Claesson, Lexington, MA (US); Matthew Fullana, Wilmington, MA (US); Gary E Wnek, Cleveland, OH (US)

(73) Assignee: Anexis, LLC, Beverly, MA (US)

(*) Notice: Subject to any disclaimer, the term of this patent is extended or adjusted under 35 U.S.C. 154(b) by 0 days.

(21) Appl. No.: 14/663,262

(22) Filed: Mar. 19, 2015

(65) Prior Publication Data

US 2016/0213814 A1  Jul. 28, 2016

Related U.S. Application Data

(60) Provisional application No. 61/968,250, filed on Mar. 20, 2014.

(51) Int. Cl.
*A61L 27/24* (2006.01)
*A61L 27/54* (2006.01)

(52) U.S. Cl.
CPC .............. *A61L 27/24* (2013.01); *A61L 27/54* (2013.01); *A61L 2430/02* (2013.01)

(58) Field of Classification Search
CPC ...................................................... A61L 27/24
See application file for complete search history.

(56) References Cited

U.S. PATENT DOCUMENTS

| | | | |
|---|---|---|---|
| 5,752,974 A | 3/1998 | Rhee | |
| 8,383,092 B2 | 2/2013 | Lee | |
| 2004/0037813 A1* | 2/2004 | Simpson | A61F 2/08 424/93.7 |
| 2005/0147643 A1 | 7/2005 | Hunter | |

FOREIGN PATENT DOCUMENTS

| | | | |
|---|---|---|---|
| CA | 2406972 A1 * | 10/2001 | ............... C08H 1/06 |
| JP | 60147487 | 8/1985 | |
| JP | 2006104178 | 4/2006 | |

OTHER PUBLICATIONS

IPRP/WO for PCT/US16/20909 dated May 31, 2016.

* cited by examiner

*Primary Examiner* — Benjamin Packard
(74) *Attorney, Agent, or Firm* — Rhodes IP PLC; Christopher R Rhodes

(57) ABSTRACT

Certain embodiments described herein are directed to cohesive materials comprising treated, derivatized collagen molecules. In some embodiments, the cohesive material can function as a putty or defect filler that can be used in a tissue repair. Methods of using the cohesive materials are also described.

10 Claims, 4 Drawing Sheets

COHESIVE MATERIALS INCLUDING DERIVATIZED COLLAGENS AND METHODS OF MAKING AND USING THEM

PRIORITY APPLICATION

This application claims priority to, and the benefit of, U.S. Provisional Application No. 61/968,250 filed on Mar. 20, 2014, the entire disclosure of which is hereby incorporated herein by reference for all purposes.

TECHNOLOGICAL FIELD

Certain features, aspects and embodiments are directed to cohesive materials produced from derivatized collagens and methods of making and use them. In particular, certain embodiments are directed to the use of alkylated collagens to provide a cohesive material.

BACKGROUND

Collagen is a protein comprising a triple helix of alpha peptides. Collagen is found in many animal tissues including connective tissue.

SUMMARY

Certain features, aspects and embodiments described herein are directed to cohesive materials produced using derivatized collagens. In some embodiments, the cohesive material can function as a pressure sensitive material that can be applied to a tissue defect site and used in a tissue repair or as a putty or filler. In some instances, the cohesive material can be produced without the use of any surfactants and/or by forming a derivatized collagen agglomerate. Illustrations of different types of collagens and their use in producing such cohesive materials are described in more detail below.

In one aspect, a cohesive material comprising derivatized collagen, e.g., agglomerated, derivatized collagen, lacking any cross-linking from an external cross-linking agent is provided. In some instances, the cohesive material effective to adhere to a mammalian tissue site, e.g., can function as a putty, filler, layer, etc.

In another aspect, a cohesive material comprises derivatized collagen, e.g., agglomerated, derivatized collagen, lacking any cross-linking from an external cross-linking agent that comprises at least two different, derivatized collagens is described. The multi-component cohesive material can be effective to adhere to a mammalian tissue site, e.g., can function as a putty, filler, layer, etc.

In a further aspect, a method of producing a cohesive material comprising adding a derivatized collagen to a solution comprising an effective amount of alcohol and aqueous salt solution to solubilize the derivatized collagen, and adding an effective amount of alcohol to the solution comprising the solubilized, derivatized collagen to produce the cohesive material is disclosed. As discussed in more detail herein, the amount of alcohol and/or salt that is effective to solubilize the derivatized collagen may depend, for example, on the amount of derivatized collagen present and the particular derivatization groups present.

In an additional aspect, a method of producing a cohesive material comprising alkylating a collagen with an alkylating group to provide an alkylated collagen, adding the alkylated collagen to a solution comprising an effective amount of alcohol and salt solution to solubilize the alkylated collagen, adding an effective amount of an alcohol to the solution comprising the solubilized, alkylated collagen to provide a cohesive material mixture and separating the collagen from the solution and the alcohol to provide a cohesive material.

In some embodiments, the derivatized collagen is methylated. In other embodiments, the derivatized collagen is alkylated. In some instances, the alkyl group comprises up to six carbons or up to ten carbons. In some embodiments, the alkyl group is unsaturated. In other embodiments, the alkyl group comprises at least one heteroatom, e.g., N, O, S, halogens or other non-carbon atoms. In some examples, the cohesive material can include at least one polymer conjugated to the derivatized collagen. In other examples, the cohesive material can include at least one pharmaceutically active compound conjugated to the derivatized collagen. In some embodiments, the cohesive material can include a second pharmaceutically active compound, different from the at least one pharmaceutically active compound, conjugated to the derivatized collagen.

In another aspect, a cohesive material comprising a methylated collagen present in an effective amount to provide a lap shear strength of at least 300 kPa as tested by ASTM D3163 (dated 2014) or other suitable tests for measuring lap shear strength is provided.

In certain examples, the methylated collagen is further derivatized. In some examples, the further derivatization comprises an alkyl group. In some embodiments, the alkyl group comprises up to six carbons or up to ten carbons. In certain examples, the alkyl group is unsaturated. In other examples, the alkyl group comprises at least one heteroatom e.g., N, O, S, halogens or other non-carbon atoms. In other embodiments, the cohesive material can include at least one polymer conjugated to the methylated collagen. In some examples, the cohesive material can include at least one pharmaceutically active compound conjugated to the methylated collagen. In additional examples, the cohesive material can include a second pharmaceutically active compound, different from the at least one pharmaceutically active compound, conjugated to the methylated collagen.

In an additional aspect, a suspension comprising a derivatized collagen in a form that permits introduction or injection of the derivatized collagen into a mammal is provided. The derivatized collagen can be suspended in a delivery fluid which may vary, though the delivery fluid typically may be a biocompatible fluid or solution that does not elicit any long-term, adverse biological response.

In some embodiments, the derivatized collagen is a methylated collagen. In other embodiments, the suspension can include a pharmaceutically active compound conjugated to the derivatized collagen. In some embodiments, the pharmaceutically active compound is a growth factor, a protein or a lipid. In some examples, the suspension can include at least one polymeric material in the delivery fluid. In other embodiments, the polymeric material is conjugated to the derivatized collagen. In some examples, the polymeric material is a polyglycol. In additional examples, a second pharmaceutically active compound, different from the pharmaceutically active compound, conjugated to the derivatized collagen can be present.

In another aspect, a composition comprising a cohesive material comprising a derivatized collagen in an ophthalmically suitable carrier effective to deliver the derivatized collagen to a mammalian eye is disclosed. In certain embodiments, the derivatized collagen is methylated. In some examples, the derivatized collagen is alkylated. In additional examples, the alkyl group comprises up to six carbons or up to ten carbons. In some examples, the alkyl group is unsaturated. In additional examples, the alkyl group comprises at least one heteroatom. In some embodiments, the composition can include at least one polymer conjugated to the derivatized collagen. In other embodiments, the composition can include at least one pharmaceutically active compound conjugated to the derivatized collagen. In additional embodiments, the composition can include a second pharmaceutically active compound, different from the at least one pharmaceutically active compound, conjugated to the derivatized collagen.

In an additional aspect, a composition comprising a derivatized collagen, e.g., a methylated collagen, in an ophthalmically suitable carrier effective to deliver the methylated collagen to a mammalian eye is described. In certain examples, the derivatized collagen is further derivatized. In other examples, the further derivatized collagen is derivatized with an alkyl group. In some embodiments, the alkyl group comprises up to six carbons or up to ten carbons. In other examples, the alkyl group is unsaturated. In some embodiments, the alkyl group comprises at least one heteroatom. In further embodiments, the composition can include at least one polymer conjugated to the methylated collagen. In additional embodiments, the composition can include at least one pharmaceutically active compound conjugated to the methylated collagen. In other embodiments, the composition can include a second pharmaceutically active compound, different from the at least one pharmaceutically active compound, conjugated to the derivatized collagen.

In another aspect, a method of treating a wound comprising disposing a cohesive material comprising a derivatized collagen on the wound to thereby treat the wound is provided. In certain embodiments, the derivatized collagen comprises a methylated collagen. In other embodiments, the derivatized collagen comprises a pharmaceutically active compound conjugated to the derivatized collagen. In additional embodiments, the pharmaceutically active compound is a growth factor, a protein, or a lipid. In some examples, the method can include adding at least one polymeric material to the derivatized collagen. In other examples, the polymeric material is conjugated to the derivatized collagen. In some embodiments, the polymeric material is a polyglycol or polyalcohol. In further embodiments, a second pharmaceutically active compound, different from the pharmaceutically active compound, can be conjugated to the derivatized collagen.

In an additional aspect, a bilayer comprising a first layer and a second layer disposed on the first layer, in which at least one of the first layer or the second layer comprises a cohesive material as described herein. In some instances, one of the first and second layers comprises a collagen scaffold and the other layer may comprise a derivatized collagen as produced herein. In certain configurations, one of the first and second layers comprises an acellular tissue implant, e.g., one of the layers comprises a derivatized collagen that has been subjected to alcohol treatment as described herein. In some embodiments, the first layer comprises a first cohesive material and the second layer comprises a second cohesive material, in which the second cohesive material is different than the first cohesive material, and in which the first and second cohesive materials are independently any of the cohesive materials described herein.

In another aspect, a tissue implant comprising a primary scaffold and a secondary scaffold, in which one of the primary scaffold and the secondary scaffold comprises one of the cohesive materials described herein is provided.

In an additional aspect, a tissue implant comprising a honeycomb material and a cohesive material (as described herein) disposed on the honeycomb material is described.

Other aspects and advantages of the present technology will become apparent to those skilled in the art, given the benefit of this disclosure, after review of the following detailed description.

BRIEF DESCRIPTION OF FIGURES

Certain examples are described below with reference to the accompanying figures in which.

DETAILED DESCRIPTION

Figure 1A:
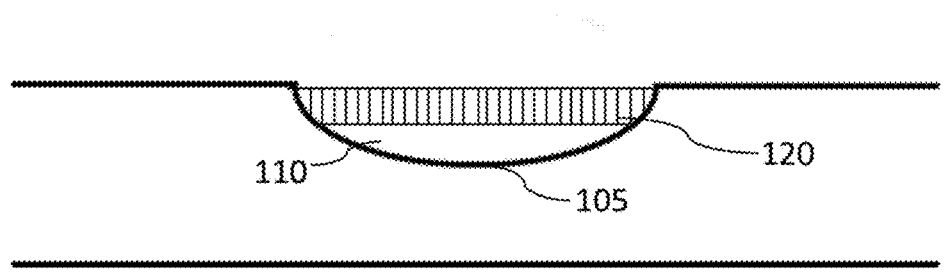
FIGS. 1A and 1B are illustrations showing use of a cohesive material with a honeycomb material, in accordance with certain examples.

It is a substantial attribute that embodiments of the cohesive materials described herein can be produced using fewer steps, simpler reactions and reduced processing time including, if desired, aseptic production methods that do not require additional sterilization steps. The cohesive materials can be used without the addition of a cross-linker or with the addition of a cross-linker. In other instances, the cohesive materials can be used with or without any cross-linking. In some instances, the cohesive materials may be produced without the use of any surfactants or detergents, which may undesirably interfere with the tissue repair process. The term "cohesive" refers to a material which can act to couple two or more other components to each other. As noted herein, the cohesive is at least partially adhesive, to at least some degree or for some period, and, depending on the composition, may be similar to a pressure sensitive adhesive. While the exact nature of the cohesive material may vary depending on the materials present, the treatment of the derivatized collagen may result in swelling of the material that acts to increase its overall stickiness. For example, swelling of the material may increase its surface area to provide more interactions with another surface on which the material is disposed. An increase in the stickiness can act to retain the material at a site.

In certain configurations, the materials described herein may be used as a filler or putty, as a loading agent or interstitial material that may be present between two or more other structures or components or as a component of a tissue implant or other composite structure that can be implanted into a subject. The cohesive materials can be present as a layer or layers, packed into a defect site, loaded into a carrier or scaffold or may be used in other manners.

Certain embodiments described herein refer to aseptic conditions or producing derivatized collagens without further purification and/or sterilization steps. Under such aseptic conditions, the cohesive material can be derivatized in a reactor or reaction cell that is sealed from the ambient environment to prevent any contamination. Reactants may be sterilized and then added to the reaction cell to provide the cohesive materials without risk of contamination. In some embodiments, a closed reaction cell circuit can be constructed where gaseous reactant is introduced into the cell by a charge and is circulated in the closed reaction cell for reaction with the collagen. Such reactants may be introduced through septa or other means in the reaction cell in a manner to avoid contamination of the reaction cell by microorganisms or other unwanted species.

Cohesives Materials and Cohesive Material Production

In certain instances described herein, one or more cohesive materials may be produced using a derivatized collagen that is produced as described herein. The cohesive material may be used without the addition of an external cross-linking agent or, if desired, can be used with an external cross-linking agent. In other instances, the cohesive material can be produced on site by mixing a suitable derivatized collagen with one or more other agents, solution or solvents to provide the cohesive material. In some instances, the cohesive material can be produced by combining a derivatized collagen with an effective amount of materials to treat and/or agglomerate the derivatized collagen. Treatment of the derivatized collagen can increase the overall stickiness and/or cohesive strength of the collagen. In some instances, the derivatized collagen can function similar to a pressure sensitive adhesive for biological applications, as noted in more detail below.

In certain instances, one or more derivatized collagens can be combined with an effective amount of an inert or non-reactive solution to promote treatment of the derivatized collagen, e.g., to promote swelling and/or to increase stickiness of the derivatized collagen. The terms "inert" or "non-reactive" refers to the materials in the solution being generally non-reactive with the derivatized collagen. The materials may interact with the collagen by way of hydrophilic or hydrophobic forces or other non-covalent bonding interactions, but the non-reactive materials desirably do not covalently react with any functional groups present on the collagen.

In some examples, the non-reactive solution may comprise one or more primary alcohols. For example, the solution may comprise methanol, ethanol, propanol, butanol, pentanol, hexanol or other primary alcohols. For example, the primary alcohol may comprise 1 to 10 carbon atoms (straight chained or branched), 1 to 6 carbon atoms (straight chained or branched) or 1 to 3 carbon atoms (straight chained or branched). In some embodiments, the primary alcohol may be a diol, triol or may otherwise include two or more —OH units. In other instances, the non-reactive solution may comprise one or more secondary alcohols. For example, the secondary alcohol may be iso-propanol, butan-2-ol, pentan-3-ol or other secondary alcohols comprising 3 to 10 carbon atoms (straight chained or branched), 3 to 8 carbon atoms (straight chained or branched) or 3 to 6 carbon atoms (straight chained or branched). In further configurations, the non-reactive solution may comprise one or more tertiary alcohols. For example, the solution may comprise t-butyl alcohol or 2-methylbutan-2-ol or other tertiary alcohols comprising 4 to 12 carbon atoms (straight chained or branched), 4 to 8 carbon atoms (straight chained or branched) or 4 to 6 carbon atoms (straight chained or branched). If desired, the solution may comprise two different generic types of alcohols, e.g., a primary alcohol and a secondary alcohol.

In certain instances, the non-reactive solution may also comprise one or more salts present in an effective amount to either solubilize the collagen or desolubilize the collagen. For example, the interaction between water molecules, salt, and alcohol can provide a derivatized collagen that is water soluble under certain conditions. Collagen is insoluble in most solvents because of interpeptide interactions. Collagen can be substantially soluble in suitable water-alcohol-salt inert solutions depending on the concentration of the various components in the solution. Illustrative salts include alkali metal salts, alkaline metal salts and halide salts, e.g., alkali halide salts, though other suitable salts that are soluble in the inert solution may also be used. As noted below, the exact concentration of salt used to solubilize the derivatized collagen can depend, for example, on the nature of the derivatized collagen and the presence of other solvents in the solution.

In certain embodiments, in some water-alcohol-salt solvents, the ratio of water to alcohol can range from a volume ratio of about 99:1 to about 1:99, the salt concentration can range from near 0 moles per liter (M) to the maximum salt concentration soluble in water, and the amount of derivatized collagen by weight (as compared to the weight of the solvent) can range from near 0 percent to about 40 percent by weight, more particularly about 9 percent to about 32 percent by weight. Where alkylated collagens are used, the weight percentage in the solution may be higher, e.g., 0-50% by weight, if desired. In one example, the non-reactive solution comprises about a one-to-one ratio of water to ethanol and a salt concentration of about 3 M NaCl. Derivatized collagen, e.g., alkylated collagen, can be added to the solution up to an amount that it starts to become insoluble, e.g., the solution may become saturated with collagen until the solubility point of collagen is reached. In one instance, the non-reactive solution may comprise phosphate buffered saline (PBS) buffer and ethanol, where the buffer to ethanol ratio is about one-to-one by volume. The saline concentration in the PBS buffer can range from 1× to 20×. For example, the solvent can comprise a PBS buffer with a salt concentration of 20× mixed with ethanol at a one-to-one ratio by volume. Illustrative solvents are described, for example, in U.S. Pat. No. 8,318,903, the entire disclosure of which is hereby incorporated herein by reference.

As will be understood by the person of ordinary skill in the art, given the benefit of this disclosure, the pH level, temperature, type of derivatized collagen, and type and concentration of salt all influence the solubility of the derivatized collagen. For example, at low non-derivatized collagen concentrations and a pH level of about 7.4, the transition temperature of crystalline polymer, e.g., a triple-helical polymer, to random coil polymer is about 45 degrees Celsius. The transition temperature can be independent of salt concentration for potassium chloride (KCl) and NaCl. The collagen solubility profile is affected by the salt content, e.g., the collagen becomes more soluble as more salt is added. Addition of salt increases the ionic strength of the treated collagen. Alcohol can affect the solubility of collagen in the buffer and ethanol solution. Alcohol and collagen interaction is moderated by hydrocarbon chain length, with alcohol disrupting internal hydrophobic interactions in the collagen. With increased alcohol concentration, there is a progressive increase in destabilization of the crystalline collagen precipitated in an alcohol and a phosphate buffer mixture at an acidic pH, for example, a pH of about 4.8. For single collagen molecules, structural stability is primarily a function of interpeptide hydrogen bonding and chain rigidity. Hydrogen bonding between the hydrophilic part of collagen and water molecules can be too weak to break the interpeptide interaction, and the stronger electrostatic forces induced by salt in aqueous media may be necessary. The combination of both electrostatic and hydrophobic forces can interact strongly enough with the collagen chain to substantially dissolve the collagen in a mixture of alcohol, e.g., ethanol, and salt buffer, e.g., PBS buffer, with an about one-to-one ratio when a salt concentration is at least about 5× in the buffer.

In addition to dissolving the derivatized collagens, the buffer and alcohol solvent can further facilitate additional processing steps such as, for example, electrospinning or drying. The salt in the buffer and/or the alcohol can assist in overcoming the high surface tension of water that can partially inhibit spinnability of water based polymeric solution. In addition, the salt increases the charge density in the protein solution, which can facilitate the formation of a stable Taylor cone. The low evaporation rate of water, which can inhibit the formation of dry fibers during electrospinning, can be compensated for by the high evaporation rate of alcohol.

In some embodiments, the derivatized collagen is added to the non-reactive solution gradually, with stirring if desired, until the collagen no longer is solubilized, e.g., the solution is saturated with the derivatized collagen. Additional derivatized collagen that is not soluble can be left in the non-reactive solution or removed. When the collagen has been solubilized in a suitable water-alcohol-salt solution, suitable perturbations can be applied to cause the derivatized collagen to agglomerate or become more sticky. In some instances, the perturbations may comprise vortexing, electrospinning, electrospraying, and/or gravitational feed methods. Other perturbations include a reduction in ionic strength by addition of more alcohols to the solution. As increased amounts of alcohol are added, the derivatized collagen can precipitate, agglomerate or fall out of solution.

In certain instances, the derivatized collagen may first be added to a non-reactive solution comprising an alcohol to solubilize the derivatized collagen. A solution of the same or different alcohol and further comprising a salt can then be added to the solubilized collagen to cause precipitation of the derivatized collagen. In some instances, addition of the inert solution comprising the salt may precipitate the derivatized collagen but not agglomerate or increase the stickiness of the derivatized collagen. To agglomerate or increase the stickiness of the derivatized collagen, an external perturbation, e.g., vortexing, electrospinning, electrospraying, reduction in ionic strength and/or gravitational feed methods, can be used to treat the derivatized collagen. Once the collagen has been treated to increase its stickiness, the non-reactive solution can be removed by decanting, lyophilization, evaporation or other means to separate the treated collagen from the solution. The separated collagen can then be dried using suitable methods, e.g., lyophilization, solvent evaporation techniques, air currents or using other suitable means.

In one example, electrospinning can be used to form treated collagen. In one instance, the electrospinning method can include placing a solution of the derivatized collagen in the non-reactive solution in a syringe. The solution in the syringe can be charged by the application of an electrical potential between a metal needle and a ground target spaced a distance away from the metal needle. The electrical potential can be applied by charging the metal needle with a voltage from a power supply. The electrical potential can be increased until the electrostatic forces in the protein solution overcome the surface tension at the tip of the metal needle. As this surface tension is overcome, a fine jet of solution containing the derivatized collagen can be drawn out of the metal needle. As the fine jet travels through the air, at least a portion (or all) of the solvent evaporates, resulting in a treated, derivatized collagen that dries (to at least some degree) as it travels through the air. The dry collagen can be collected on a surface that is in contact with the ground target or the surface itself may act as a ground and collect the fibers. The electrical potential can be created using a direct current (DC) power supply or an alternating current (AC) power supply.

In one instance, a derivatized collagen solution can be placed in a 5 milliliter (ml) syringe equipped with a 21 gauge blunt needle. The syringe can be placed in a syringe pump. A rotating drum can be placed approximately 10 centimeters (cm) from the tip of the needle. The pump rate can be set to about 1 milliliter per hour (ml/h) and the electrical potential can be set to about 20 kilovolts (kV). This setup can be used, if desired, to eventually form a cohesive material as noted herein, e.g., by using the above setup in combination with alcohol/salt treatment and/or precipitation of the material to provide a cohesive material. The electrospinning process parameters, such as flow rate, potential field, and needle-to-collector distance can be adjusted to produce a variety of results or to optimize the stability of the fine jet of solution during electrospinning. In some instances, the cohesive material can be removed from the surface by scraping or suspension in a solvent.

In some embodiments, the cohesive material can be used without the addition of an external cross-linker. For example, the cohesive material can be added to a tissue site and used to provide adherence between two or more tissue structures (or two or more other structures) to adhere some other component or material to the tissue defect site. In some embodiments, external pressure application provided to the cohesive material can act to increase the overall adhesive nature of the cohesive. In some instances, pressure can be applied by way of a mechanical device, physical stimulus, sound waves, heat or other mechanical or physical stimulus. In other instances, the pressure can be applied by movement or rotation of the physical structure bearing the tissue defect. For example, where the defect is in the knee, the knee can be rotated to permit the knee structures to apply pressure to the adhesive and increase the overall adherence of the cohesive material.

Derivatizing Agents

In certain embodiments, the most abundant functional moieties found in collagen are amine and carboxylic acid functionalities. Chemical modification of both the amine and carboxylic acid moieties can be performed. Common methods of functionalizing collagen include methylation of the carboxylic acids and succinylation of the amines. Methylation can be performed by reacting a carboxylic acid group of the collagen with methanol under acidic conditions. Succinylation of the amines can be performed under basic conditions utilizing succinic anhydride or other suitable succinylating agents. The modification of either group affects the isoelectric point of the collagen and its solubility profile. In most instances, native collagen is insoluble at physiological conditions, whereas methylated and succinylated collagens are generally soluble under physiological conditions. Such derivatization may be very useful for certain applications such as when increased adherence is desired. The presence of a net charge under physiological conditions may also be beneficial for interaction with cells and tissues. Even though the modification of collagen can have a significant impact on physical properties, such modified collagens can still retain its biological functionality.

In certain embodiments, the term "derivatized collagen" as used herein refers to collagen that has been chemically or physically altered in some manner including, but not limited to, addition of one or more moieties to the collagen, removal of one or more moieties from the collagen, internal chemical alterations of the collagen itself without addition of a non-native moiety, e.g., formation or removal of one or more disulfide bonds, double bonds, etc. and other chemical modifications. As a subset of "derivatized collagen," the collagen can be alkylated, acylated, substituted, dehydrated after derivatization or otherwise altered in some manner. In certain embodiments, the derivatized collagens described herein can be provided by reacting a suitable form of collagen with a desired amount of a derivatizing agent. The resulting products may be purified prior to use or can be used immediately without any further purification or sterilization steps. Examples of derivatizing agents, collagens, reaction conditions and applications using derivatized collagens are described below.

In certain embodiments, the derivatized collagens for use in the cohesive materials described herein can be produced by reacting one or more collagens with a suitable derivatizing agent which may be a pharmaceutically active compound or a pharmaceutically inactive compound. In some embodiments, the derivatizing agent includes at least one carbon atom and a suitable reactive group that can react with one or more groups present in the collagen. For example, the derivatizing agent can include a hydroxyl group, an amino group or both that can react with a suitable group present on the collagen to couple the derivatizing agent to the collagen. In some embodiments, the derivatizing agent can take the form of an alkylating agent, e.g., an agent that can add a methyl group or other alkyl group to the collagen. In other instances, one or more alkanolamines can be used as a derivatizing agent, e.g., methanolamine, ethanolamine, propanolamine or other alkanolamines comprising a primary amino group and 1 to 6, 1 to 4 or 1 to 3 carbon atoms. Alkylated collagens may be particularly desirable due to their potential for improved solubility in a variety of common solvents, the potential for more facile formulation with drugs and various other small-molecule and/or macromolecular additives, and the potential for good mechanical properties resulting from intermolecular interactions between alkyl groups, especially alkyl groups of sufficient length to promote hydrophobic association in aqueous solutions and even crystallization-induced aggregation. Also, the adhesive properties of such modified collagens can be tuned by judicious choice of alkyl-based functional groups, e.g., alkyl groups including long hydrocarbon chains, and spacing of the functional groups along the collagen polymer chain.

In some embodiments, more than a single type of derivatizing agent can be used. For example, collagen can first be reacted with a first derivatizing agent and then subsequently reacted with a second derivatizing agent. In other embodiments, the same derivatizing agent can be used, but it may be reacted sequentially with the collagen molecule or reacted in selected stoichiometric amounts with the collagen to derivatize a desired proportion of the collagen. In some embodiments, the collagen may first be derivatized with a lower molecular weight alkyl chain and then subsequently reacted with a higher molecular weight alkyl chain to increase the overall hydrophobicity of the derivatized collagen. In other embodiments, the collagen can first be reacted with a lower molecular weight alkyl chain and subsequently reacted with a different group, e.g., a pharmaceutically active compound or a biological agent such as, for example, a peptide, protein, carbohydrate, lipid or other biological agents.

In certain embodiments, the derivatizing agent can be an alkylating agent having one to six carbon atoms including, but not limited to, straight chain, branched and cyclic alkylating agents with one to six carbon atoms. Where 5 or 6 carbon atoms are present, the alkylating agent can be a fully saturated cyclic compound, a cyclic compound with one or more sites of unsaturation, or an aromatic compound. In other embodiments, the alkylating agent can include one carbon, one to two carbons, one to three carbons, one to four carbons, or one to five carbons. In some examples, the alkylating agent can include two carbons, two to three carbons, two to four carbons, two to five carbons or two to six carbons. In other examples, the alkylating agent can include three carbons, three to four carbons, three to five carbons, or three to six carbons. In certain examples, the alkylating agent can include four carbons, four to five carbons or four to six carbons. In some embodiments, the alkylating agent can include five carbons or five to six carbons. In other embodiments, the alkylating agent can include six carbons. The alkylating agents described herein may be fully saturated or may be present in unsaturated form, e.g., may include one or more double or triple bonds. In some instances herein, alkylating agents including one to six carbon atoms are referred to as "lower weight alkylating agents."

In certain embodiments, the alkylating agent can include six to ten carbons. Alkylating agents with six to ten carbon atoms are sometimes referred to herein as "middle weight alkylating agents." In certain examples, the alkylating agent can include six to nine carbons, six to eight carbons, or six to seven carbons. In other embodiments, the alkylating agent can include seven to ten carbons, seven to nine carbons or seven to eight carbons. In further embodiments, the alkylating agent can include eight to ten carbons or eight to nine carbons. In other examples, the alkylating agent can include nine carbon atoms or ten carbon atoms. The middle weight alkylating agents described herein may be fully saturated or may be present in unsaturated form, e.g., may include one or more double or triple bonds.

In other embodiments, the alkylating agent can be selected to include more than ten carbon atoms to provide a hydrophobic, derivatized collagen. Alkylating agents including more than ten carbon atoms are referred to herein in certain instances as "high weight alkylating agents." The hydrophobic derivatized collagens are generally more hydrophobic than native collagen and can be adherent, at least to some degree, to permit use of the derivatized collagen in wound repair, defect repair, skin grafts, as scaffolds to attract cells and permit colonization by cells or other uses. Due to the sticky nature of certain collagens after derivatizing with an alkylating agent, they can also be used as glues or adhesives, or when used as an implant or scaffold can be used without an additional adhesive. As noted herein, overall stickiness of the derivatized collagen can be increased by subjecting the collagen to further treatment, e.g., alcohol and/or salt treatment as noted herein.

In certain examples, where the alkylating agent includes more than ten carbon atoms, it may include ten to twenty four carbons, ten to twenty-two carbons, ten to twenty carbons, ten to eighteen carbons, ten to sixteen carbons, ten to fourteen carbons or ten to twelve carbons and include both saturated and unsaturated forms thereof. In other embodiments, the alkylating agent can include twelve to twenty four carbons, twelve to twenty-two carbons, twelve to twenty carbons, twelve to eighteen carbons, twelve to sixteen carbons, or twelve to fourteen carbons and include both saturated and unsaturated forms thereof. In further embodiments, the alkylating agent can include fourteen to twenty four carbons, fourteen to twenty-two carbons, fourteen to twenty carbons, fourteen to eighteen carbons, or fourteen to sixteen carbons and include both saturated and unsaturated forms thereof. In additional embodiments, the alkylating agent can include sixteen to twenty four carbons, sixteen to twenty-two carbons, sixteen to twenty carbons, or sixteen to eighteen and include both saturated and unsaturated forms thereof. In other embodiments, the alkylating agent can include eighteen to twenty four carbons, eighteen to twenty-two carbons, or eighteen to twenty carbons and include both saturated and unsaturated forms thereof. In some embodiments, the alkylating agent can include twenty to twenty four carbons or, twenty to twenty-two carbons and include both saturated and unsaturated forms thereof.

In some embodiments, the alkylating agent comprises at least one terminal reactive group, e.g., a terminal hydroxyl group or terminal amino group. In other embodiments, the alkylating agent comprises at least one internal reactive group, e.g., a hydroxyl group or amino group not present at a terminus of the alkylating agent. In some embodiments, the alkylating agent can be a compound of formula (1)

 (1)

where $R_1$ may be hydroxyl, amino, acyl, or benzoyl. In other embodiments, $R_1$ includes at least one carbon atom, e.g., 1 to 6 carbon atoms, in addition to a non-carbon atom such as, for example, hydrogen, nitrogen or sulfur. In some embodiments, $R_1$ can be $HOCH_2$—, $HOCH_2CH_2$— or $HO(CH_2)_n$— where n is three to ten, more particularly, three to nine, three to eight, three to seven, three to six, three to five, or three to four, five, six, seven, eight, nine or ten. In some embodiments, $R_1$ of formula (1) is hydroxyl (—OH), a primary amine (—NH$_2$) or may be a secondary amine, a diamine or a sulfhydryl group (—SH).

In other embodiments, the alkylating agent can be one or more of the compounds of formula (2)

 (2)

where $R_2$ may be hydroxyl, amino, acyl or benzoyl and n can be 1, 2, 3, 4, 5, or 6. In some embodiments, n is 1 and $R_2$ is hydroxyl, e.g., —OH. In other embodiments, n is 2 and $R_2$ is hydroxyl. In further embodiments, n is 3 and $R_2$ is hydroxyl. In additional embodiments, n is 4 and $R_2$ is hydroxyl. In additional embodiments, n is 5 and $R_2$ is hydroxyl. In some embodiments, n is 1 and $R_2$ is amino, e.g., —NH$_2$. In other embodiments, n is 2 and $R_2$ is amino. In further embodiments, n is 3 and $R_2$ is amino. In additional embodiments, n is 4 and $R_2$ is amino. In additional embodiments, n is 5 and $R_2$ is amino. If desired, where $R_2$ is amino, the amino group may be a secondary amine or a tertiary amine instead of a primary amine.

In certain embodiments, the alkylating agent can be selected as a compound of formula (3)

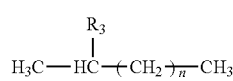 (3)

where $R_3$ may be hydroxyl, amino, acyl or benzoyl and n can be 1, 2, 3, 4, 5 or 6. In some embodiments, n is 1 and $R_3$ is hydroxyl, e.g., —OH. In other embodiments, n is 2 and $R_3$ is hydroxyl. In further embodiments, n is 3 and $R_3$ is hydroxyl. In additional embodiments, n is 4 and $R_3$ is hydroxyl. In additional embodiments, n is 5 and $R_3$ is hydroxyl. In some embodiments, n is 1 and $R_3$ is amino, e.g., —NH$_2$. In other embodiments, n is 2 and $R_3$ is amino. In further embodiments, n is 3 and $R_3$ is amino. In additional embodiments, n is 4 and $R_3$ is amino. In additional embodiments, n is 5 and $R_3$ is amino. If desired, where $R_2$ is amino, the amino group may be a secondary amine or a tertiary amine instead of a primary amine.

In some embodiments, the derivatizing agent can be a compound having formula (4)

 (4)

where $R_2$ of formula (4) may be any of those groups listed for $R_2$ of formula (2) and n is 1, 2, 3, 4, 5 or 6. $R_4$ can methoxy, ethoxy, oxypropyl, hydroxyl, amino, acyl, benzoyl, aryl, naphthyl or carboxyl (—COOH). In some embodiments, each of $R_2$ and $R_4$ is hydroxyl and n is 2, 3, 4, 5, or 6. In other embodiments, one of $R_2$ and $R_4$ is hydroxyl and the other of $R_2$ and $R_4$ is amino and n is 2, 3, 4, 5 or 6.

In other embodiments, the derivatizing agent can be a compound having formula (5)

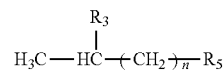 (5)

where $R_3$ of formula (5) may be any of those groups listed for $R_3$ of formula (3) and n is 1, 2, 3, 4, 5 or 6. $R_5$ can methoxy, ethoxy, oxypropyl, hydroxyl, amino, acyl, benzoyl, aryl, naphthyl or carboxyl. In some embodiments, each of $R_3$ and $R_5$ can be hydroxyl or one of $R_3$ and $R_5$ is hydroxyl and the other one of $R_3$ and $R_5$ is amino.

In other embodiments, the alkylating agent may be a compound of formula (6)

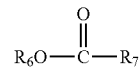 (6)

where $R_6$ can be hydrogen or a hydrocarbon chain (saturated or unsaturated) having 1 to 4 carbon atoms which may be branched if desired. In some embodiments, $R_7$ comprises 1 to 6 carbons (saturated and unsaturated forms). In other embodiments, $R_7$ may be a hydrocarbon chain (saturated or unsaturated) including 7-10 carbons. In further embodiments, $R_7$ may be a hydrocarbon chain (saturated or unsaturated) including ten to twenty four carbon atoms. In some embodiments, $R_6$ is hydrogen and $R_7$ is selected to provide compound (6) that is one of dodecanoic acid, tetradecanoic acid, hexadecanoic acid, octadecanoic acid, eicosanoic acid, tetracosanoic acid, 9-hexadecenoic acid, 9-octadecenoic acid, 9,12 octadecadienoic acid, 9,12,15-octadecatrienoic acid, 6,9,12-octadecatrienoic aid, 5,8,11,14-eicosatetraenoic acid or 15-tetracosenoic acid. In some embodiments, $R_7$ can have a formula of $CH_3(CH)_n$— where n can be nine to about twenty-three. In other embodiments, $R_7$ can have a formula of $CH_3(CH)_n$—C=O where n can be nine to about twenty-three. In some embodiments, $R_6$ is hydrogen and $R_7$ is any one of the groups listed above for $R_7$.

In other embodiments, the alkylating agent may be a compound of formula (7)

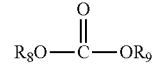 (7)

where $R_8$ can be hydrogen or a hydrocarbon chain (saturated or unsaturated) having 1 to 4 carbon atoms which may be branched if desired, and $R_9$ may be a hydrocarbon chain (saturated or unsaturated) including ten to twenty four carbon atoms. In some embodiments, $R_9$ can have a formula of $CH_3(CH)_n$— where n can be nine to about twenty-three. In other embodiments, $R_9$ can have a formula of $CH_3$ $(CH)_n$—C=O where n can be nine to about twenty-three. In some embodiments, each of $R_8$ and $R_9$ is hydrogen. In other embodiments, $R_8$ is hydrogen and $R_9$ may be any of the groups listed above for $R_9$.

In certain embodiments, the derivatized collagen may be a methylated collagen comprising one or more methyl groups added to the collagen at a suitable site. For example, the derivatized collagen may be methylated at one or more carboxyl groups to provide an ester. In some embodiments, enough derivatizing agent is present such that substantially all free and accessible carboxyl sites of the collagen react with the derivatizing agent to form an ester comprising a methoxy group covalently bonded to the carbonyl group of the ester.

In other embodiments, the derivatizing agent to provide methylation (or other alkylation or derivatization) can be selected such that free carboxyl groups remain in the collagen molecule subsequent to reaction with the derivatizing agent. By using selected amounts of the derivatizing agent, free reactive groups remain post-derivatization to permit reaction with other agents.

In certain embodiments, a pharmaceutically active compound can be reacted with the derivatized collagen molecule to conjugate the active compound to the collagen. This conjugation is typically performed prior to agglomerization of the collagen in the inert solution. In some instances, the pharmaceutically active compound make take the form of a biological agent or compound, e.g., a peptide, protein, carbohydrate, lipid or the like, that can be conjugated to the derivatized collagens described herein. Illustrations of pharmaceutically active compounds are described in more detail below. In certain examples, a pharmaceutically active compound is a chemical compound, e.g., natural or synthetic, that can elicit a biological response, e.g., activate a cellular response or pathway, inhibit a cellular response or pathway, promote a cellular response or pathway, or alter a cellular response or pathway, under suitable conditions. For example, a pharmaceutically active compound can result in activation (or inactivation) of a cellular pathway, enzyme activation, enzyme inhibition, differentiation of a stem cell into a desired cell type, repair of a tissues, cellular enhancement, inhibition of cellular processes, activation (or deactivation) of an ion channel, an increase (or decrease) in protein expression, an increase (or decrease) in RNA production, an increase (or decrease) in mitosis, an increase (or decrease) in meiosis, an increase (or decrease) in intracellular transport, or other activities that a cell may perform or initiate through one or more cellular systems or pathways. Without wishing to be bound by any particular theory, hydrophobic pharmaceutically active compounds can be solubilized in hydrophobic domains of alkylated collagen, the latter acting as reservoirs for such compounds. Such configurations may be particularly useful to deliver drugs topically, e.g., to the skin, mouth, nose, digestive tract, or eyes.

In certain examples, when a pharmaceutically active compound is present as a conjugate with a derivatized collagen, e.g., a methylated collagen, it may be present in an effective amount, e.g., an amount effective to elicit the biological response. In some configurations, the concentration of pharmaceutically active compound may exceed the amount desired to elicit a biological response such that sustained release of the pharmaceutically active compound can provide for such biological response for extended periods. It will be recognized by the person of ordinary skill in the art, given the benefit of this disclosure, that there are multiple ways to provide an effective amount of the pharmaceutically active compound. In some embodiments, the pharmaceutically effective amount can be provided by including a plurality of the pharmaceutically active compounds on the derivatized collagen helix, e.g., by including large numbers of conjugated active compound per collagen helix an effective amount can be provided using fewer collagen helices, whereas in other examples the concentration of the derivatized collagen/conjugated compound can be selected to provide the effective amount.

In certain embodiments, the pharmaceutically active compound may be a non-synthetic pharmaceutically active compound whereas in other examples the pharmaceutically active compound may be a synthetic compound. Non-synthetic compounds include, but are not limited to, natural products and naturally occurring compounds. Synthetic compounds include analogs of non-synthetic pharmaceutically active compounds and other compounds not existing naturally or not yet found to exist naturally. Where a non-synthetic pharmaceutically active compound is conjugated to a derivatized collagen, the compound itself may be produced chemically, e.g., using total synthesis, even though the non-synthetic pharmaceutically active compound is naturally occurring. If desired, both a non-synthetic and synthetic pharmaceutically active compound may be conjugated to the derivatized collagen, e.g., to the methylated collagen.

In certain embodiments, the pharmaceutically active compound may be a protein, a carbohydrate, a lipid, a peptide, an amino acid, a nucleoside, a nitrogenous base, a nucleoside phosphate, an interference RNA (RNAi), a steroid, a high energy phosphate, a high energy biomolecule, an enzyme or other compounds, materials or components commonly present in one or more metabolic pathways of a cell.

In certain examples, the derivatized collagens described herein, e.g., methylated collagens, can be conjugated to a growth factor such as, for example, adrenomedullin (AM), autocrine motility factor, a bone morphogenetic protein (BMP), a brain-derived neurotrophic factor (BDNF), an epidermal growth factor (EGF), erythropoietin (EPO), a fibroblast growth factor (FGF), a glial cell line-derived neurotrophic factor (GDNF), a granulocyte colony-stimulating factor (G-CSF), a granulocyte macrophage colony-stimulating factor (GM-CSF), a growth differentiation factor-9 (GDF9), a hepatocyte growth factor (HGF), a hepatoma-derived growth factor (HDGF), an insulin-like growth factor (IGF), a migration-stimulating factor, myostatin (GDF-8), a nerve growth factor (NGF) and other neurotrophins, a platelet-derived growth factor (PDGF), thrombopoietin (TPO), a transforming growth factor alpha (TGF-α), a transforming growth factor beta (TGF-β), a tumor necrosis factor-alpha (TNF-α), a vascular endothelial growth factor (VEGF), a Wnt Signaling Pathway protein, a placental growth factor (PlGF), a fetal bovine somatotrophin (FBS), IL-1-Cofactor for IL-3 and IL-6, IL-2-T-cell growth factor, IL-3, IL-4, IL-5, IL-6, IL-7 or other suitable growth factors. In some examples, any growth factor which can activate (or inhibit if desired) a kinase pathway, e.g., MAP kinase, PI3 kinase or the like, can be conjugated to the derivatized collagen. While the exact chemistry used to couple the growth factor to the derivatized collagen can vary, in many instances a free amino group of the growth factor can be coupled to a free carboxyl group of the collagen to provide an amide bond between the derivatized collagen and the growth factor. Alternatively, a free carboxyl group of the growth factor can be coupled to a group of the collagen. Where no such groups are present on the growth factor, the growth factor can be derivatized using one or more activating agents, e.g., a carbodiimide, a succinyl group, etc., and then reacted with a group present in the derivatized collagen.

In other configurations, the derivatized collagen can be conjugated to one or more therapeutics such as those described in *Goodman and Gilman's the Pharmacological Basis of Therapeutics*. Where a therapeutic is present, the therapeutic may be used alone as a pharmaceutically active compound or with another pharmaceutically active compound such as, for example, a growth factor or other selected active compound. Illustrative therapeutic agents include but are not limited to a neurotransmitter, a cholinase activator or inhibitor, an acetylcholinesterase activator or inhibitor, an acetylcholine, an acetylcholine agonist or derivative, a nicotinic receptor agonist, a nicotinic receptor antagonist, a muscarinic receptor agonist, a muscarinic receptor antagonist, dopamine, a dopamine derivative, a catecholamine, an adrenergic receptor agonist, an adrenergic receptor antagonist, an anticholinesterase agent, a nicotinic cholinergic receptor agonist, a nicotinic cholinergic receptor antagonist, a ganglionic blocking compound, a ganglionic stimulant, a serotonin receptor agonist, a serotonin receptor antagonist, an ion channel agonist, an ion channel antagonist, a neuromodulator, a therapeutic gas (e.g., oxygen, carbon dioxide, nitric oxide), ethanol or an ethanol derivative, a benzodiazepine analog, a phenothiazine, a thioxanthene, a heterocyclic compound, a sedative, a norepinephrine reuptake inhibitor, an antidepressant, a serotonin reuptake inhibitor, a monoamine oxidase agonist, a monoamine oxidase antagonist, a sodium ion channel activator, a sodium ion channel inhibitor, a calcium ion channel activator, a calcium ion channel inhibitor, a hydantoin, a barbituate, a stilbene, an iminostilbene, a succinimide, an oxazolidinedione, an antiseizure agent, an analgesic, an opioid, a peptide, an opioid agonist, an opioid antagonist, an autocoid, histamine, a histamine analog, a H1-receptor agonist, a H1-receptor antagonist, a H3-receptor agonist, a H3-receptor antagonist, an eicosanoid, a prostaglandin, a leukotriene, an anti-inflammatory agent, an antipyretic, a nonsteroidal anti-inflammatory agent, a salicylic acid derivative, a salicylate, a para-aminophenol derivative, an indole, an indene, an indole acetic acid, an indene acetic acid, a heteroaryl acetic acid, a propionic acid, an arylpropionic acid, an anthranilic acid, an enolic acid, an alkanone, an oxicam, gold and gold derivatives, a uricosuric agent, a corticosteroid, a bronchodilator, a diuretic, a vasopressin receptor agonist, a vasopressin receptor antagonist, angiotensin, an angiotensin analog, renin, a renin analog, an inhibitor of the renin-angiotensin system, an angiotensin receptor agonist, an angiotensin receptor antagonist, a renin inhibitor, an endopeptidase inhibitor, an organic nitrate, a calcium channel blocker, a beta-adrenergic receptor antagonist, an alpha-adrenergic receptor antagonist, an antiplatelet agent, an antithrombotic agent, an antihypertensive, a benzothiadiazine, a sympatholytic agent, a vasodilator, an angiotensin converting enzyme inhibitor, an angiotensin II receptor antagonist, a cardiac glycoside, a dopaminergic receptor agonist, a phosphodiesterase inhibitor, an antiarrhythmic drug, an HMG CoA reductase inhibitor, an H2 histamine receptor antagonist, an antibiotic, a hydrogen-potassium ATPase inhibitor, an antacid, a laxative, an antidiarrheal agent, an antiemetic agent, a prokinetic agent, oxytocin, an antimalarial agent, a diaminopyrimidine, quinine and quinine derivatives, quinoline and quinoline derivatives, an antihelminthic agent, an antimicrobial agent, a sulfonamide, a quinolone, a penicillin, a cephalosporin, a beta-lactam, an aminoglycoside, a tetracycline, a chloramphenicol, an erythromycin, an isonicotinic acid compound and derivatives thereof, a macrolide, a sulfone, an antifungal agent, an imidozole, a triazole, an antiviral agent, a protease inhibitor, an antiretroviral agent, a reverse transcriptase inhibitor, an acyclic nucleoside phosphonate, a nitrogen mustard, an ethylenimine, a methylmelamine, an alkyl sulfonate, a nitrosourea, a triazene, a folic acid analog, a pyrimidine analog, a purine analog, a vinca alkaloid, an epipodophyllotoxin, a coordination complex, a platinum coordination complex, an anthracenedione, a substituted urea, a methylhydrazine derivative, an adrenocortical suppressant, a progestin, an estrogen, an anti-estrogen, an androgen, an anti-androgen, a gonadotropin-releasing hormone analog, an immunosuppressant, an interferon, a granulocyte macrophage-colony stimulating factor, a tumor necrosis factor, an interleukin, an antibody, an antigen, a hematopoietic agent, an anticoagulant, a hormone, a growth hormone, a glucocorticoid, an antiseptic, insulin, a hypoglycemic agent, a hyperglycemic agent, an insulin analog, a vitamin, a water soluble vitamin, a fat soluble vitamin, a skin agent, an ocular agent, a cosmetic agent, a heavy metal antagonist, or other suitable synthetic or non-synthetic therapeutics. Where a therapeutic agent is present, it may be present alone or in combination with a biomolecule or another pharmaceutically active compound.

In some embodiments, the derivatized collagen described herein can include more than a single type of pharmaceutically active compound conjugated to it. For example, the derivatized collagen can first be reacted with a growth factor and subsequently reacted with a different pharmaceutically active compound to provide a hybrid derivatized collagen comprising more than a single type of pharmaceutically active compound. The derivatized collagen may then be further processed to provide a cohesive.

Collagens

The particular form of collagen selected for use in producing the cohesive material comprising a derivatized collagen can vary depending on the desired end product. In some embodiments, collagen obtained from any source, including both naturally occurring collagens and synthetic collagens, can be derivatized using the methods and derivatizing agents described herein. For example, collagen may be extracted and purified from human or other animal sources, e.g., mammalian sources, such as bovine or porcine, or may be recombinantly produced, synthetically produced by chemical synthesis or otherwise produced using selected techniques. Collagen of any type, including, but not limited to, types I-IV or any combination thereof, may be reacted with a derivatizing agent as described herein. In some embodiments, type I collagen is reacted with one or more derivatizing agents. In other embodiments, atelopeptide collagen or telopeptide-containing collagen may be used. Atelopeptide collagen may include desirable attributes including reduced immunogenicity when compared to telopeptide-containing collagen. In some embodiments, the collagen can be a Type I collagen, a Type II collagen, a Type III collagen, a Type IV collagen, a gelatin, a collagen comprising agarose, a collagen comprising hyaluronan, a collagen comprising proteoglycan, a glycosaminoglycan, a glycoprotein, glucosamine or galactosamine, a collagen comprising fibronectin, a collagen comprising laminin, a collagen comprising a bioactive peptide growth factor, a collagen comprising a cytokine, a collagen comprising elastin, a collagen comprising fibrin, a collagen comprising polylactic, polyglycolic or polyamino acid, a collagen comprising polycaprolactone, collagen comprising a polypeptide, or a copolymer thereof, each alone or in combination. In other examples, the collagen can be prepared from, or can include, collagen precursors, such as, for example, peptide monomers, alpha 1 (type I), and alpha 2 (type I) collagen peptide or alpha 1 (type I) alpha 2 (type I) peptides, alone or in combination, or from a combination of precursors, such as 2 (alpha 1, type I) peptide and 1 (alpha 2, type I) peptide. If desired, the derivatized collagens can be used with other compounds, such as pharmaceutically acceptable excipients, surfactants, buffers, additives and other biocompatible components.

In certain embodiments, a non-crosslinked collagen may be reacted with one or more derivatizing agents. For example, collagen that has not been previously crosslinked by methods such as, for example, heat, irradiation, or chemical crosslinking agents can be reacted with a derivatizing agent. Subsequent to derivatization, the collagen can be cross-linked if desired. In other embodiments, cross-linked collagen can be reacted with one or more of the derivatizing agents described herein. For example, atelopeptide collagen can be crosslinked using heat, irradiation, or chemical crosslinking agents, and the resulting cross-linked product may then be reacted by addition of a suitable amount of derivatizing agent to the solution.

While certain embodiments herein describe the use of intact collagen, denatured collagen, commonly known as gelatin, can also be used if desired. In some embodiments, a mixture of intact collagen and denatured collagen can be reacted with a derivatizing agent, and the resulting products can be used, for example, as described herein.

In certain embodiments, the collagen can be extracted and purified from human tissue, e.g., placenta or other human tissue. In some embodiments, the collagen may be chorion and/or amnion collagen. The amnion/chorion can be isolated from other placental tissues, homogenized, digested with proteases, reconstituted. In other embodiments, the collagen can be a non-antigenic collagen in solution from mammalian skin, e.g., bovine skin or porcine skin. In other embodiments, the collagen can be prepared by washing placentas in acid/ethanol to remove blood and extraneous debris. The washed placental tissue can then be treated with a protease, e.g., pepsin at a low pH of about 2-3 to solubilize the collagen. The solubilized collagen can then be treated with a series of salt fractionations at acid and neutral pH to reduce the type III content of the collagen to below about 10% by weight. The type I-enriched collagen can be solubilized in acid, then filtered and reconstituted from solution. Additional washing steps such as, for example, washing with acetone, can be performed. The resulting collagen powder can be solubilized in acid and sterile-filtered. If desired, the collagen can be precipitated from the sterile filtered solution and resuspended in a suitable solvent.

In other embodiments, either fibrillar or non-fibrillar collagen (as present in its native environment) can be used as a starting material and reacted with a derivatizing agent. Non-fibrillar collagen can be more tacky than fibrillar collagen and may be desirable for use where the resulting derivatized collagen is adherent, to at least some degree. Non-fibrillar collagens refers to any modified or unmodified collagen material that is in substantially non-fibrillar form at pH 7, as indicated, for example, by optical clarity of an aqueous suspension of the collagen. Collagen types that are non-fibrillar (or microfibrillar) in native form include, for example, types IV, VI, and VII. In some embodiments, fibrillar collagen can be used but rendered non-fibrillar prior to reaction with a derivatizing agent. For example, chaotropic agents, surfactants, detergents, alcohols, salts, etc. can be added to disassemble the fibers from the collagen and provide non-fibrillar collagen. In some examples, fibrillar collagen can be reacted with a derivatizing agent. Fibrillar collagen has desirable attributes in certain applications including the ability to form more cross-linked compositions compared to certain forms of non-fibrillar collagens.

In some instances, acid swollen collagen may also be used. Derivatized acid swollen collagen may provide greater cohesive strength and is typically inexpensive. Acid swollen collagen consists, for example, of bovine corium in the native state. The bovine corium consist of predominantly Type I collagen with about 5% Type III collagen.

In certain examples, the derivatized collagens described herein can be used with, or can be conjugated to, one or more biocompatible polymers. A biocompatible polymer is any polymeric material that does not adversely affect cell or tissue function in a non-desired manner. Illustrative biocompatible polymers can be non-synthetic or synthetic. Illustrative types of biocompatible polymers suitable for use with, or suitable for conjugation to, the derivatized collagens described herein include but are not limited to, agarose, hyaluronic acid, alginic acid, dextrans, polyHEMA, polyglycols (including, for example, polyethylene glycol), a polyalcohol, and poly-vinyl alcohol alone and combinations and derivative forms thereof. If desired, the polymers can be cross-linked using physical means, e.g., light or ionizing radiation, or chemical cross-linking agents. In some embodiments, the derivatized collagen can be cross-linked to the biocompatible polymer, if desired. In certain embodiments, the derivatized collagen may be used with, or may be conjugated to, one or more other polymeric materials including, but not limited to, polyvinyl alcohol (PVA), polyethylene glycol (PEG), polyvinyl pyrrolidone (PVP), polyacrylamide (PA), polyhydroxyethyl methacrylate (PHEMA), and copolymers of any of them, chitosan, agarose, dextran, alginic acid, hyaluronic acid and gelatin, as well as an interpenetrating network (hydrogels such as, for example), gelatin crosslinked with poly(ethylene glycol) diacrylate or other suitable polymeric species. In some embodiments, the derivatized collagen can be conjugated to one or more monomer units, including but not limited to, ethylene oxide, vinyl alcohol, (meth)acrylamide, N-alkylated (meth)acrylamides, N-methylol(meth)acrylamide, N-vinylamides, N-vinylformamide, N-vinylacetamide, N-vinyl-N-methylacetamide, N-vinyl-N-methylformamide, hydroxyalkyl (meth)acrylates such as hydroxyethylmethacrylate, vinylpyrrolidone, (meth)acrylic esters of polyethylene glycol monoallyl ethers, allyl ethers, of polyethylene glycols, and sugar units such as glucose, fructose, sucrose or galactose. Illustrative additional types of monomer units include, but are not limited to, ethyleneimine (in the protonated form), diallyldimethylammonium chloride and trimethylammonium propylmethacrylamide chloride, (meth)acrylic acid, crotonic acid, maleic acid, fumaric acid, itaconic acid, 2-acrylamido-2-methylpropanesulfonic acid, vinylsulfonic acid, vinylphosphonic acid, 2-methacryloyloxyethanesulfonic acid, 4-vinylbenzenesulfonic acid, allylsulfonic acid, vinyltoluenesulfonic acid and vinylbenzenephosphonic acid. In some examples, the polymer conjugated to the derivatized collagen can include both hydrophilic units and hydrophobic units or a mixture of hydrophilic chains and hydrophobic chains as desired.

In certain examples, the overall molecular weight of the derivatized collagens, including any conjugated pharmaceutically active compounds and/or conjugated polymers, may be selected based on the desired use of the derivatized collagen. For example, depending on the desired hydrophobicity, adherence strength or other physical properties, the molecular weight of the derivatized collagen can be increased. To reduce the overall molecular weight, the derivatized collagen can be subjected to shear stress to fragment the collagen helices into lower molecular weight helices. Fragmented helices may be destabilized, and where fragmentation is performed the fragmentation desirably does not break the collagen to too high of a degree. The fragmented helices may then be reacted with one or more derivatizing agents to provide a derivatized collagen. In other instances, the derivatized collagen may be fragmented post-derivatization, and the resulting combination of fragments can be used without further separation or desired fragment sizes may be isolated prior to use, e.g., using size-exclusion chromatography or other suitable methods.

In certain embodiments, additional materials can be included or used with the derivatized collagens described herein. For example, the derivatized collagens can be used with preservatives, anti-oxidants, imaging agents, stabilizers, colorants, fibers, powders, whiskers, metal particles, sols, gels, hydrogels or other selected compounds that can provide a desired result.

Derivitization Conditions

By using one or more of the derivatizing agents described herein, considerably shorter processing times, simplified work-up steps and aseptic production can be implemented if desired. While the exact reaction conditions may vary depending on the particular derivatizing agent selected, the production scheme generally involves subjecting collagen to a derivatizing agent under suitable reaction conditions. For example, the derivatizing agent can be reacted with the collagen under acidic conditions, neutral conditions or basic conditions depending on the form of collagen selected and/or the nature of the derivatizing agent.

In some embodiments, the derivatizing agent can react with a carboxyl group of the collagen to provide an ester. The derivatizing agent can be, for example, an alcohol, e.g., may be one of compounds of formula (1)-(7) where an OH group is present, and the R group of the derivatizing agent forms a bond with a carbonyl group of the collagen to derivatize the collagen with the R group and form an ester.

In other embodiments, a free amine group of collagen can be reacted with a derivatizing agent to provide a derivatized collagen. The free amine group can be present in the collagen itself or a free amine group may be added to the collagen from a first derivatizing agent, e.g., using an alkanolamine. In many instances, desired amine/carboxylic acid reactions are preceded by acid/base reactions forming salts that require high temperatures for conversion to amides with dehydration. Such high temperatures are undesirable with reactions on, for example, collagen, proteins and/or thermally labile therapeutic agents. To avoid the high temperatures commonly associated with such reactions, amine groups can react cleanly and under very mild conditions with activated carboxylic acids. While the particular activating agent can vary, a N-hydroxysuccinimidyl (NHS) group as shown in compound (8) is often used to facilitate reaction between an amino group and a carboxylic acid or other species including a carbonyl group.

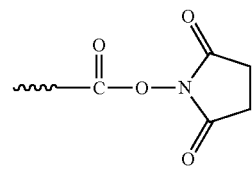

(8)

By reacting a derivatizing agent that has been activated with NHS, the derivatizing agent can be coupled to the collagen molecule through an amine group of the collagen to provide the derivatized collagen with an activated acid group that can form an amide bond. In some embodiments, derivatizing agent may be added to the collagen at both carbonyl sites and amino sites. Where such reactions are performed, the particular group added to a carbonyl group of the collagen may be the same or may be different than the group added to the amino group of the collagen. In some instances, an alcohol form of the derivatizing agent may be reacted with the collagen in the presence of a NHS activated derivatizing agent to reduce the overall reaction time and to decrease the number of work up steps to provide the derivatized collagen.

In certain embodiments, the reactions described herein can be used to conjugate a pharmaceutically active compound to the collagen molecule. In some instances, the collagen may already be derivatized at certain sites, e.g., methylated at one or more sites, and the pharmaceutically active compound can be conjugated to a free site on the derivatized collagen by reacting a free hydroxyl group of the pharmaceutically active compound with a carbonyl group of the collagen molecule, by reacting an amino group of the pharmaceutically active compound with a carbonyl group of the collagen molecule or by reacting an activated form of the pharmaceutically active compound, e.g., a NHS activated form, with the collagen molecule. In some embodiments, the pharmaceutically active compound can be first reacted with a linker or coupling agent, e.g., using carbodiimides such as EDC, to provide a desired reactive group on the pharmaceutically active compound for reaction with one or more free sites of the collagen molecule. In some embodiments, the linking group may be a spacer that provides for more ready access to the pharmaceutically active compound by an enzyme or other biologically active species. For example, the spacer may be a short hydrocarbon chain including 1-6 carbon atoms that becomes bonded to a carbonyl group or an amino group of the collagen molecule after reaction of the pharmaceutically active compound with the derivatized collagen.

In other embodiments, the collagen can first be alkylated with a derivatizing agent through one or more carbonyl groups (or other groups) of the collagen molecule. The alkylated collagen can then be reacted to provide an activated acid group to permit further derivatizion of the alkylated collagen. If desired, one or more free amino groups of the collagen (or a free amino group added to the collagen) may then be reacted with another agent to form an amide bond between the collagen and the other agent.

In one embodiment, collagen can be precipitated by creating physiological conditions in the solution, and then centrifuging the collagen. The resulting pelletized collagen can be placed in methanol to remove residual moisture, and lyophilization may be performed to remove any solvent and water. The lyophilized collagen can be placed into a solvent comprising the derivatizing agent in an acidic environment overnight, e.g., placed in 100 mM aqueous HCl. Residual liquid may be removed, and the solution can be neutralized using a suitable base such as NaOH. The neutralized derivatized collagen can be lyophilized for storage or resuspended in a selected solvent. Where the process is performed under aseptic conditions, no sterilization of the resulting derivatized collagen need be performed. If sterilization is performed, ion beam, electron beam or other suitable sterilization methods can be performed.

In another embodiment, the lyophilized collagen can be exposed to gaseous derivatizing agent in an acidic environment overnight, e.g., exposed to the gaseous derivatizing agent in the presence of gaseous HCl. The gaseous, acidic environment can be replaced with an inert gas such as nitrogen for long term storage. The derivatized collagen can be stored or resuspended in a selected solvent. Where the process is performed under aseptic conditions, no sterilization of the resulting derivatized collagen need be performed. If sterilization is performed, ion beam, electron beam or other suitable sterilization methods can be performed.

Cohesive Material Loading

In some instances, rather than react the collagen with a bioactive substance to derivatize the collagen with the bioactive substance, the collagen can be derivatized with an alkyl group (or other suitable group), and a cohesive material can be produced as noted herein, e.g., by treating the derivatized collagen using a non-reactive solution comprising salt/alcohol. In some examples, one or more pharmaceutically active compounds or substances or materials can then be mixed with the cohesive material prior to use. The sticky nature of the cohesive material acts to retain the materials for at least some period. In particular, where the cohesive material is loaded with a pharmaceutically active compound or material, the two materials are not cross-linked to each other but remain together for at least some period. The pharmaceutically active compound may become trapped in the collagen helices or may loosely associate with or to the collagen helices by way of hydrophilic or hydrophobic bonding, for example.

In some instances, the pharmaceutically active compound make take the form of a biological agent or compound, e.g., a peptide, protein, carbohydrate, lipid or the like, that can be combined with the cohesive as described herein. Illustrations of pharmaceutically active compounds suitable for mixing or combining with the cohesive are described in more detail below. In certain examples, a pharmaceutically active compound is a chemical compound, e.g., natural or synthetic, that can elicit a biological response, e.g., activate a cellular response or pathway, inhibit a cellular response or pathway, promote a cellular response or pathway, or alter a cellular response or pathway, under suitable conditions. For example, a pharmaceutically active compound can result in activation (or inactivation) of a cellular pathway, enzyme activation, enzyme inhibition, differentiation of a stem cell into a desired cell type, repair of a tissues, cellular enhancement, inhibition of cellular processes, activation (or deactivation) of an ion channel, an increase (or decrease) in protein expression, an increase (or decrease) in RNA production, an increase (or decrease) in mitosis, an increase (or decrease) in meiosis, an increase (or decrease) in intracellular transport, or other activities that a cell may perform or initiate through one or more cellular systems or pathways.

In certain examples, when a pharmaceutically active compound is present in a mixture with the cohesive material, it may be present in an effective amount, e.g., an amount effective to elicit the biological response. In some configurations, the concentration of pharmaceutically active compound may exceed the amount desired to elicit a biological response such that sustained release of the pharmaceutically active compound can provide for such biological response for extended periods. It will be recognized by the person of ordinary skill in the art, given the benefit of this disclosure, that there are multiple ways to provide an effective amount of the pharmaceutically active compound. In some embodiments, the pharmaceutically effective amount can be provided by including a plurality of the pharmaceutically active compounds in the presence of the cohesive material.

In certain embodiments, the pharmaceutically active compound mixed with the cohesive material may be a non-synthetic pharmaceutically active compound whereas in other examples the pharmaceutically active compound may be a synthetic compound. Non-synthetic compounds include, but are not limited to, natural products and naturally occurring compounds. Synthetic compounds include analogs of non-synthetic pharmaceutically active compounds and other compounds not existing naturally or not yet found to exist naturally. Where a non-synthetic pharmaceutically active compound is combined with a cohesive material, the compound itself may be produced chemically, e.g., using total synthesis, even though the non-synthetic pharmaceutically active compound is naturally occurring. If desired, both a non-synthetic and synthetic pharmaceutically active compound may be combined with the cohesive material.

In certain embodiments, the pharmaceutically active compound may be a protein, a carbohydrate, a lipid, a peptide, an amino acid, a nucleoside, a nitrogenous base, a nucleoside phosphate, an interference RNA (RNAi), a steroid, a high energy phosphate, a high energy biomolecule, an enzyme or other compounds, materials or components commonly present in one or more metabolic pathways of a cell.

In certain examples, the derivatized collagens described herein, e.g., methylated collagens, can be used to produce a cohesive material that is combined with a growth factor such as, for example, adrenomedullin (AM), autocrine motility factor, a bone morphogenetic protein (BMP), a brain-derived neurotrophic factor (BDNF), an epidermal growth factor (EGF), erythropoietin (EPO), a fibroblast growth factor (FGF), a glial cell line-derived neurotrophic factor (GDNF), a granulocyte colony-stimulating factor (G-CSF), a granulocyte macrophage colony-stimulating factor (GM-CSF), a growth differentiation factor-9 (GDF9), a hepatocyte growth factor (HGF), a hepatoma-derived growth factor (HDGF), an insulin-like growth factor (IGF), a migration-stimulating factor, myostatin (GDF-8), a nerve growth factor (NGF) and other neurotrophins, a platelet-derived growth factor (PDGF), thrombopoietin (TPO), a transforming growth factor alpha(TGF-α), a transforming growth factor beta(TGF-β), a tumor necrosis factor-alpha (TNF-α), a vascular endothelial growth factor (VEGF), a Wnt Signaling Pathway protein, a placental growth factor (PlGF), a fetal bovine somatotrophin (FBS), IL-1-Cofactor for IL-3 and IL-6, IL-2-T-cell growth factor, IL-3, IL-4, IL-5, IL-6, IL-7 or other suitable growth factors. In some examples, any growth factor which can activate (or inhibit if desired) a kinase pathway, e.g., MAP kinase, PI3 kinase or the like, can be mixed with the cohesive.

In other configurations, the cohesive material can be combined with one or more therapeutics such as those described in *Goodman and Gilman's the Pharmacological Basis of Therapeutics*. Where a therapeutic is present, the therapeutic may be used alone as a pharmaceutically active compound or with another pharmaceutically active compound such as, for example, a growth factor or other selected active compound. Illustrative therapeutic agents include but are not limited to a neurotransmitter, a cholinase activator or inhibitor, an acetylcholinesterase activator or inhibitor, an acetylcholine, an acetylcholine agonist or derivative, a nicotinic receptor agonist, a nicotinic receptor antagonist, a muscarinic receptor agonist, a muscarinic receptor antagonist, dopamine, a dopamine derivative, a catecholamine, an adrenergic receptor agonist, an adrenergic receptor antagonist, an anticholinesterase agent, a nicotinic cholinergic receptor agonist, a nicotinic cholinergic receptor antagonist, a ganglionic blocking compound, a ganglionic stimulant, a serotonin receptor agonist, a serotonin receptor antagonist, an ion channel agonist, an ion channel antagonist, a neuromodulator, a therapeutic gas (e.g., oxygen, carbon dioxide, nitric oxide), ethanol or an ethanol derivative, a benzodiazepine analog, a phenothiazine, a thioxanthene, a heterocyclic compound, a sedative, a norepinephrine reuptake inhibitor, an antidepressant, a serotonin reuptake inhibitor, a monoamine oxidase agonist, a monoamine oxidase antagonist, a sodium ion channel activator, a sodium ion channel inhibitor, a calcium ion channel activator, a calcium ion channel inhibitor, a hydantoin, a barbituate, a stilbene, an iminostilbene, a succinimide, an oxazolidinedione, an antiseizure agent, an analgesic, an opioid, a peptide, an opioid agonist, an opioid antagonist, an autocoid, histamine, a histamine analog, a H1-receptor agonist, a H1-receptor antagonist, a H3-receptor agonist, a H3-receptor antagonist, an eicosanoid, a prostaglandin, a leukotriene, an anti-inflammatory agent, an antipyretic, a nonsteroidal anti-inflammatory agent, a salicylic acid derivative, a salicylate, a para-aminophenol derivative, an indole, an indene, an indole acetic acid, an indene acetic acid, a heteroaryl acetic acid, a propionic acid, an arylpropionic acid, an anthranilic acid, an enolic acid, an alkanone, an oxicam, gold and gold derivatives, a uricosuric agent, a corticosteroid, a bronchodilator, a diuretic, a vasopressin receptor agonist, a vasopressin receptor antagonist, angiotensin, an angiotensin analog, renin, a renin analog, an inhibitor of the renin-angiotensin system, an angiotensin receptor agonist, an angiotensin receptor antagonist, a renin inhibitor, an endopeptidase inhibitor, an organic nitrate, a calcium channel blocker, a beta-adrenergic receptor antagonist, an alpha-adrenergic receptor antagonist, an antiplatelet agent, an antithrombotic agent, an antihypertensive, a benzothiadiazine, a sympatholytic agent, a vasodilator, an angiotensin converting enzyme inhibitor, an angiotensin II receptor antagonist, a cardiac glycoside, a dopaminergic receptor agonist, a phosphodiesterase inhibitor, an antiarrhythmic drug, an HMG CoA reductase inhibitor, an H2 histamine receptor antagonist, an antibiotic, a hydrogen-potassium ATPase inhibitor, an antacid, a laxative, an antidiarrheal agent, an antiemetic agent, a prokinetic agent, oxytocin, an antimalarial agent, a diaminopyrimidine, quinine and quinine derivatives, quinoline and quinoline derivatives, an antihelminthic agent, an antimicrobial agent, a sulfonamide, a quinolone, a penicillin, a cephalosporin, a beta-lactam, an aminoglycoside, a tetracycline, a chloramphenicol, an erythromycin, an isonicotinic acid compound and derivatives thereof, a macrolide, a sulfone, an antifungal agent, an imidozole, a triazole, an antiviral agent, a protease inhibitor, an antiretroviral agent, a reverse transcriptase inhibitor, an acyclic nucleoside phosphonate, a nitrogen mustard, an ethylenimine, a methylmelamine, an alkyl sulfonate, a nitrosourea, a triazene, a folic acid analog, a pyrimidine analog, a purine analog, a vinca alkaloid, an epipodophyllotoxin, a coordination complex, a platinum coordination complex, an anthracenedione, a substituted urea, a methylhydrazine derivative, an adrenocortical suppressant, a progestin, an estrogen, an anti-estrogen, an androgen, an anti-androgen, a gonadotropin-releasing hormone analog, an immunosuppressant, an interferon, a granulocyte macrophage-colony stimulating factor, a tumor necrosis factor, an interleukin, an antibody, an antigen, a hematopoietic agent, an anticoagulant, a hormone, a growth hormone, a glucocorticoid, an antiseptic, insulin, a hypoglycemic agent, a hyperglycemic agent, an insulin analog, a vitamin, a water soluble vitamin, a fat soluble vitamin, a skin agent, an ocular agent, a cosmetic agent, a heavy metal antagonist, or other suitable synthetic or non-synthetic therapeutics. Where a therapeutic agent is present, it may be present alone or in combination with a biomolecule or another pharmaceutically active compound.

Applications and Uses

The cohesive materials described herein can be used as a component in tissue repair procedures and constructs. It may be lyophilized as an aqueous solution or phase separated from the solvent. In some embodiments, the cohesive material may be used in combination with a scaffold or network that permits infiltration and growth of cells in one-dimensional, two-dimensional of multi-dimensional arrangement. To increase the overall strength of the scaffold, reinforcing fibers, particles, powders, whiskers or the like can be used in combination with the cohesive. If desired, the cohesive material can be used with support materials, e.g., meshes, stents, screens or the like, to provide increased rigidity. In some embodiments, the support material can be absorbable or degradable such that they disappear or are absorbed slowly, whereas in other examples the support material may be resistant to degradation.

In certain embodiments, the cohesive materials described herein can be used with one or more cells, cell lysates, cell homogenates, cell aspirates or other suitable cell extracts or cell preparations. In some embodiments, the cohesive materials can be used in combination with a plurality of stem cells. In additional examples, the cohesive materials can be used in combination with a plurality of bone precursor cells. In other examples, the cohesive materials can be used with a plurality of epithelial cells.

In some examples, the cohesive materials can be used with (or as a component of) a bioactive scaffold that promotes repair and regeneration through sequestering and mechanically supporting cells. The bioactive scaffolds can be configured to encapsulate molecules (either autogenous or exogenous) which act as inducers of tissue regeneration, while allowing for the sustained release of such healing molecules. In other embodiments, the bioactive scaffolds may be effective to cause patients' cells to be stimulated and migrate into the scaffold on a concentration gradient. The bioactive scaffold may also be effective to assist migrated cells of varying degrees of pluripotency to differentiate into tissue-specific cells. In other instances, the bioactive scaffold may mimic the structural support of the tissue while healing is occurring, and, if desired, for an appropriate length of time for the given tissue being regenerated, becoming harmlessly absorbed by the body. The cohesive material can be used to hold the bioactive scaffold in place (for at least some period) or can be used as a gel or gel-like substance to permit loading of materials into the bioactive scaffold. In other instances, the cohesive material can be used to load materials into the bioactive scaffold. For example, one or more pharmaceutically active compounds can be mixed with a cohesive material and the mixture can be loaded into the bioactive scaffold by diffusion or other means. In certain embodiments, a bioactive scaffold can include other components as well. For example, bioactive scaffolds can be produced from a derivatized collagen and a non-derivatized collagen. If desired, the scaffold can be derivatized to improve tissue regeneration, by sequestering and releasing, small-molecule regeneration promoters such as (2S)-1-(1,2-dioxo-3,3-dimethylpentyl)-2-pyrrolidine carboxylic acid and other versions of RIL (Regenerative Immunophilic Ligands). These small molecules can be reacted with amine groups or other groups, and the combination of a natural biopolymer such as a methylated collagen with such compounds is particularly attractive in the broad area of regenerative medicine, especially wound healing. If desired, other small molecules can be used in conjunction with derivatized collagen scaffolds to promote the selective differentiation of mesenchymal stem cells (MSC) into specific tissue forming and generating cells. For example chondrocytes can be stimulated to form hyaline cartilage tissue in such a scaffold by such molecules as Kartogenin (*Science*. 2012 May 11; 336(6082):717-21), and utilized in osteoarthritic tissue and injured cartilage lesion regeneration. Promoting its selectively local use can be promoted by using it in conjunction with a derivatized collagen scaffold. Another means of getting cells to grow and differentiate on a derivatized collagen scaffold is to alter the nano-structure of the scaffold by use of a procedure that allows for greater numbers of cells to grow and differentiate on the surface of the scaffold.

In certain examples, the cohesive materials described herein can be used in combination with one or more electroprocessed collagens, sponges, matrices or materials. For example, the derivatized collagens described herein can be used with one or more materials described in U.S. Pat. Nos. 7,734,774, 7,615,373, 7,759,082 or published U.S. Patent Application Nos. 20040058887, 20040018226 and 20020081732, the entire disclosure of each of which is hereby incorporated herein by reference.

In some embodiments, the cohesive materials described herein can be effective to stick to one or more anatomical sites within a mammal. The cohesive material is generally sticky to adhere to all tissues including but not limited to bone, skin, muscle, nerves and cardiovascular organs and structures, and therefore improve their ability to act as carriers of healing agents, small molecules, biologicals, tissue-specific cells, pluripotent cells, multipotent cells, and inducers of tissue creation of all types. The cohesive material can be used alone or in combination with other polymeric materials to alter its adhesive properties. In some instances, the cohesive material is added without the use of any external cross-linking agent. In some embodiments, the cohesive material may be cross-linked with an additional material immediately prior to use or during use to alter the physical properties of the cohesive material. For example, partial esterification of the collagen of the cohesive material, leaving sites for NHS incorporation, could help modulate adhesion and permit subsequent reaction with other species. In some embodiments, the cohesive material comprising collagen can be cross-linked after placement at an anatomical site using UV light irradiation, chemical cross-linking agents, changes in pH, heat or other physical or chemical means.

In other embodiments, the cohesive materials described herein can be used with a pharmaceutically active compound as a drug delivery device. Where the cohesive material is configured as a drug delivery device, it may be effective to retain the pharmaceutically active compound for at least some period and provide for release, e.g., immediate release or sustained release, of the pharmaceutically active compound. In some embodiments, the cohesive material can be designed to retain the pharmaceutically active compound until a change in ionic strength of the surrounding environment results in a change in the three-dimensional structure of the cohesive and subsequent release of the pharmaceutically active compound. For example, the cohesive/retained pharmaceutically active compound can be placed on a wound or other site within a mammal. The surrounding environment in the mammal may result in a change in the tertiary or quaternary structure of the cohesive, e.g., association of the hydrophobic helices of the collagen with each other, and provide release of the pharmaceutically active compound to the surrounding environment.

In certain examples, the cohesive materials described herein may be selected to be optically transparent so that can be used in ophthalmic applications. For example, the cohesive material can be used to provide cells, e.g., retina cells or retina precursor cells, to treat degenerative diseases of the retina. In other embodiments, the cohesive material can be used to deliver ophthalmically active compounds, e.g., compounds used to treat eye dryness, diseases of the cornea or lens or other diseases of the eye.

In some embodiments, the cohesive materials described herein can be used in topical applications, e.g., applied to the skin, muscle, teeth or other tissue, to provide a desired result. In some embodiments, the cohesive materials may include one or more agents designed to provide an aesthetic or cosmetic effect. For example, the cohesive materials may include whitening or bleaching agents that can increase the whiteness of the teeth when applied. The stickiness of the cohesive materials may increase their overall retention on the teeth. In other embodiments, the cohesive materials may include a cream, emollient, or other skin healing agent that can assist in removal of skin discolorations or other unwanted skin conditions. In some instances, the hydrophobic nature of the cohesive materials permits use in treating infection of the nails such as, for example, toe nail fungal infections. Topical application of the cohesive materials can form a strip or patch that sticks to the nail and can provide a desired release of an anti-fungal compound, e.g., griseofulvin, terbinafine or the like, to the nail. Additionally, the hydrophobic nature of the cohesive materials may assist in penetration of the nail surface to provide for more effective delivery of the anti-fungal.

In certain embodiments, the cohesive materials described herein can be used as an injectable material for aesthetic rejuvenation. For example, the cohesive materials can be designed to be substantially non-resorbable or biodegradable and can be injected into the face or other areas of the body for cosmetic purposes. Alternatively, agents such as Botox® cosmetic can be included in the cohesive materials or conjugated to the cohesive materials to provide for sustained release of the agents subsequent to injection.

In certain embodiments, the cohesive materials described herein can be used in one or more layers of a bilayer. For example, a cohesive material may be disposed on a tissue defect site as a layer followed by deposition of a scaffold or tissue implant. In some instances, the bilayer may comprise two or more different cohesive materials described herein, with a first layer comprising a first cohesive material and a second layer comprising a second cohesive material different from the first cohesive material. In other configurations, one of the cohesive materials described herein is present in a first layer, and a collagen scaffold or collagen tissue implant is then disposed on the cohesive material as the second layer of the bilayer. One or both layers of the bilayer may be loaded with a therapeutic or biologically active molecule. For example, a cohesive material comprising methylated collagen (or alkylated collagen) can be loaded with demineralized bone powder (treated to retain the BMP's) and used as a layer facing the osteo-arthritic bone.

Figure 1B:
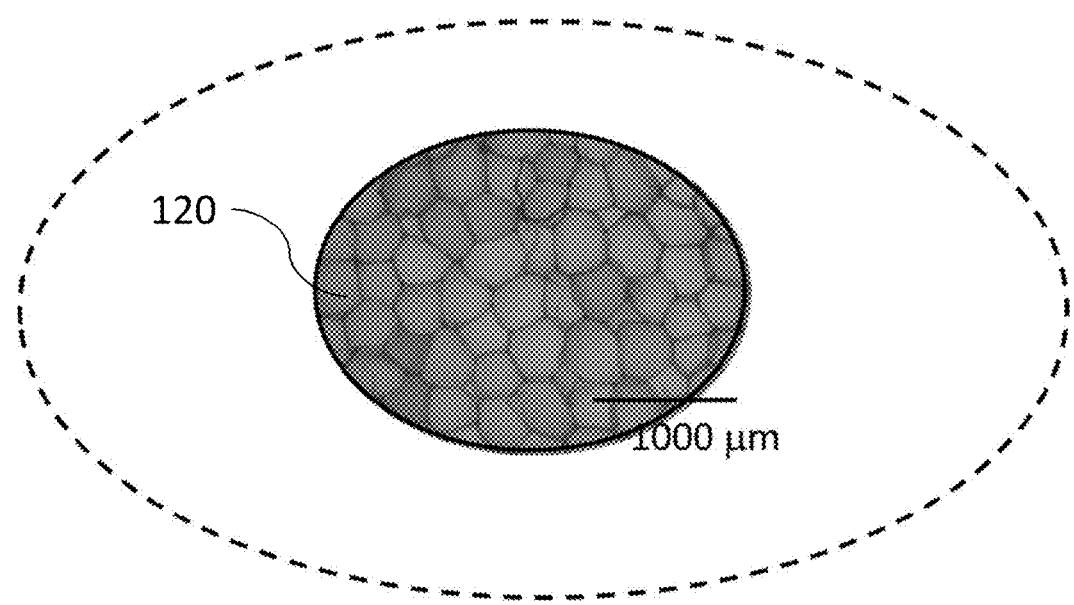

A scaffold or tissue implant (as noted below) comprising honeycomb material may be disposed on the cohesive material layer to heal cartilage and may comprise bone marrow aspirate or centrifuged aspirate or pluripotent cells from the patient's fatty tissue. This bilayer can be used, for example, to treat sport induced osteochondral lesions. The bi-layered scaffold covers a large area and the layer facing the bone, as it regels, slowly releases the BMP's to stimulate new bone production. The honeycomb layer contains pluripotent cells and can be used for the cartilage repair. Referring to FIGS. 1A and 1B, an illustration of a bi-layer structure is shown that comprises a cohesive material 110 disposed on a tissue 105, which may be bone or other tissues. A honeycomb material 120 (as described herein and as graphically shown in the top view of FIG. 1B) may be disposed on the cohesive material 110. While not shown, a sealant may be disposed on the honeycomb material 120 if desired. The cohesive material may be loaded with one or more materials, e.g., demineralized bone powder in the case where tissue 105 is bone, to permit release of the materials into the tissue 105. In some instances, the cohesive material 110 can be loaded into the honeycomb material prior to disposal of the honeycomb material onto the tissue 105. Cells or other materials can also be loaded into the cohesive material prior to loading the cohesive material into the honeycomb.

In some embodiments, the cohesive materials described herein can be used with or as part of a tissue implant (TI) which may include, for example, a first scaffold and a second scaffold. In certain configurations, the TI can have improved properties compared to a single scaffold implant and provides for variability in use. The TI may include, for example, a primary collagen-based structure, hereinafter called a primary scaffold, and a secondary collagen-based structure, hereinafter called a secondary scaffold. The two scaffolds are structurally and functionally different. Each scaffold can be prepared from a different collagen-based composition with the primary scaffold prepared first and the secondary scaffold prepared by introducing a different collagen-based composition within the primary scaffold thereby forming a composite structure comprising the primary scaffold incorporated with a solution comprising a collagen, e.g., a derivatized collagen, in a basic solution (typically in the absence of any surfactant) for preparation of said secondary scaffold. If desired, one or more of the cohesive materials described herein can be used as or with the primary scaffold or the secondary scaffold. The composite structure can then be subjected to a lyophilization and dehydrothermal treatment processes. In one configuration, the primary scaffold may comprise a derivatized collagen as described in commonly owned U.S. application Ser. No. 14/506,744 filed on Oct. 6, 2014, the entire disclosure of which is hereby incorporated herein by reference in its entirety. In other instances, the secondary scaffold may be a derivatized collagen as described in commonly owned U.S. application Ser. No. 14/506,744. In additional configurations, each of the primary scaffold and the secondary scaffold may be a derivatized collagen as described in commonly owned U.S. application Ser. No. 14/506,744, with the primary scaffold and the secondary scaffold comprising at least one different derivatized collagen. The resulting TI comprises a structurally different secondary scaffold incorporated into and localized within pores of the primary scaffold.

In some instances, the TI can be used in tissue repair procedure. For example, before implanting, the surgeon cuts the piece of the implant and trims it to a size and shape corresponding to the size and shape of the defect or lesion, places the precut section into the defect and rehydrates the implant with sterile phosphate buffered saline or another physiologically acceptable solution optionally containing cells, such as chondrocytes, fibroblasts, mesenchymal stem cells, bone marrow aspirate, bone marrow stem cells or any other cells, cell suspensions or solutions containing growth hormone, mediators, drugs, etc., as appropriate. Alternatively, such rehydration may be performed before implanting said implant into the defect. The precut implant is suitable for placement within a full thickness defect of a tissue, and particularly for placement into an articular cartilage lesion. Once in place, the TI can be held in place by suture, biologically acceptable adhesive or a combination of both. In one instance, a cohesive material as described herein can be used to hold the TI in place by first placing a layer of the cohesive material between the TI and the tissue.

In some instances, the TI can be shipped or provided as a dry sterile product enclosed in a shipping container within sterile packaging. The packaged product is available as an off-the-shelf TI for implantation in clinical settings. Alternatively, the TI may be prepared in a sterile wet rehydrated form optionally containing cells, drugs or modulators and delivered to a surgeon in a ready-to-use form. As noted above, the TI can comprise two separately prepared components, e.g., a primary scaffold that provides a structural support for a secondary scaffold incorporated within the primary scaffold. Each of the materials used in the primary scaffold and the secondary scaffold can be or may comprise one or more of the cohesive materials described herein.

In certain embodiments, the primary scaffold can be a collagen-based matrix prepared as a honeycomb, lattice, sponge or any other similar structure made of a biocompatible and/or biodegradable collagen containing material of defined density and porosity that is pliable, storable and, most importantly, highly porous. The primary scaffold may be, or may comprise, an alcohol treated, derivatized collagen that is present as a cohesive material. Typically, the primary scaffold is prepared from collagen, collagen-containing compositions or collagen containing a polymer. Representative compounds suitable for preparation of the primary scaffold are a Type I collagen, Type II collagen, Type III collagen, Type IV, Type VI collagen, gelatin, collagen containing agarose, collagen containing hyaluronan, collagen containing proteoglycan, collagen containing glycosaminoglycan, collagen containing glycoprotein, collagen containing glucosamine, collagen containing galactosamine, collagen containing fibronectin, collagen containing laminin, collagen containing a bioactive peptide growth factor, collagen containing cytokine, collagen containing elastin, collagen containing fibrin, collagen containing polylactic, polyglycolic or polyamino acid, collagen containing polycaprolactone, collagen containing polypeptide, or a copolymer thereof, each alone or in combination with other collagen, such as Type IX and XI. If desired, any of the above materials can be first derivatized with an agent as described herein and then be treated with an alcohol/salt solution to provide a cohesive material for use in the primary scaffold. Additionally, the primary scaffold may be prepared from the collagen precursors, such as, for example, peptide monomers, such as alpha 1 (type I), and alpha 2 (type I) collagen peptide or alpha 1 (type I) alpha 2 (type I) peptides, alone or in combination, or from a combination of precursors, such as 2 (alpha 1, type I) peptide and 1 (alpha 2, type I) peptide. Further, the primary scaffold may be prepared from combinations or mixtures of various collagen, derivatized collagens or collagen precursors The collagen containing material used for preparation of the primary scaffold may further be supplemented with other compounds, such as pharmaceutically acceptable excipients, surfactants, buffers, additives and other biocompatible components. In some instances, the primary scaffold prepared from collagen and most preferably from Type I collagen (or derivatized Type I collagen such as alkylated or methylated Type I collagen) or from a composition containing Type I collagen (or derivatized Type I collagen such as methylated Type I collagen).

In some configurations, the primary scaffold can provide a structure comprising a plurality of narrowly defined randomly or non-randomly organized pores having a substantially homogeneous narrowly defined size and diameter that are uniformly distributed through the primary scaffold, dividing the primary scaffold space into columns or a pore network. In certain instances, the pores are through and mostly vertically oriented, and represent a high percentage of the total volume of the scaffold. One illustrative primary scaffold is described, for example, in U.S. application Ser. No. 11/523,833, filed on Sep. 19, 2006, which is incorporated herein by reference. In another configuration, the primary scaffold may be the Type I collagen-based support matrix that is a collagen-based porous honeycomb, sponge, lattice, sponge-like structure or honeycomb-like lattice of defined porosity having randomly or non-randomly organized pores of variable pore diameters such as described in, for example, described in U.S. Pat. No. 7,217,294, which is incorporated herein by reference. In yet another embodiment the primary scaffold is, or may include, a honeycomb collagen matrix developed by Koken Company, Ltd., Tokyo, Japan, under the trade name Honeycomb Sponge, as described in the Japanese patent JP3170693, which is incorporated herein by reference. If desired, the primary scaffold can be loaded with a cohesive material as described herein. The primary scaffold may comprise a substantially defined pore size in diameter and pore density in randomly or non-randomly organized manner that creates an apical (top) or basal (bottom) surface to the implant where the sizes and diameters of the pores on both the apical or basal surface are substantially the same, that is, at least 70% of the pores have the same size and diameter. When used as a primary scaffold only, the scaffold provides conditions for a sterically-enhanced enablement of cells. Chondrocytes, for example, can produce an extracellular matrix comprising glycosaminoglycan and Type II collagen within said implant in ratios characteristic for a normal healthy articular cartilage.

In certain examples, a secondary scaffold structure can be generated within the pores of the primary scaffold. In some instances, the primary scaffold can be loaded with a basic solution suitable for preparation of the secondary scaffold. Such a basic solution may comprise a soluble derivatized collagen, collagen-containing or collagen-like mixture, typically of Type I collagen, in combination with a polyol, e.g., polyglycol or a polyalcohol, or other desired materials. In some instances, the basic solution is prepared as a solution, suspension or as an aqueous gel at a dilute acidic pH and is further neutralized to pH 7.4. The basic solution is then applied to or is loaded into the primary scaffold such that it fills the porous structure of the primary scaffold. In some instances, the secondary scaffold can be formed by loading an ethanol/salt treated, derivatized collagen as described herein into the primary scaffold and permitting formation of a secondary scaffold.

In certain embodiments, the secondary scaffold can be created or generated within the pores of the primary scaffold. The secondary scaffold is a qualitatively different structure formed within the confines of the first scaffold or as a stand-alone unit. The secondary scaffold can be produced, for example, by a process comprising preparing a soluble collagen-based composition as described herein or by preparing a treated, derivatized collagen as described herein. The secondary scaffold comprises a collagen, alkylated collagen, methylated collagen or other derivatized collagen, gelatin or methylated gelatin, collagen-containing and collagen-like mixtures, said collagen being typically of Type I or Type II, each alone, in admixture, or in combination with other components such as a polyol, polyalcohol or alcohol. Additionally, the secondary scaffold may be used independently of the primary scaffold as the secondary scaffold stand-alone implant or unit where the basic solution can be introduced into a mold or container and subjected to precipitation, lyophilization and dehydrothermal treatment.

In preparation of the TI, a composition suitable for generation of the secondary scaffold within the primary scaffold is brought into contact with a primary scaffold structure by absorbing, wicking, soaking or by using a pressure, vacuum, pumping or electrophoresis, etc., to introduce said composition for the secondary scaffold into the pores of the primary scaffold. In an alternative configuration, the primary scaffold may be immersed into the basic solution comprising materials used to provide the secondary scaffold. In certain embodiments, the TI is prepared by treating the primary scaffold loaded with a basic solution comprising a combination of the soluble collagen (or soluble derivatized collagen) and other components. For example, the primary scaffold is loaded with the collagen, precipitated, gelled, washed, dried, lyophilized and dehydrothermally treated to solidify and stabilize the secondary scaffold within the pores of the primary scaffold. In certain instances, the cohesive materials described herein may be present in a solution that can be loaded into the primary scaffold to form a secondary scaffold.

In certain examples, the TI can be seeded with cells, loaded with pharmaceutical agents, drugs or growth modulators. For example, the primary scaffold and the secondary scaffold, can each be independently loaded with living cells, a cell suspension, with a pharmaceutically effective agent or agents or with growth modulators. These may be loaded into the implant individually or in any possible combination, such as, for example, where the cells may be introduced into one component, for example, into the primary scaffold of the TI, and the drug is introduced into the second component, for example, into the secondary scaffold of the TI, or the drug is introduced into one component and the modulator into the second component and/or any variation thereof. Both components of the TI may be loaded with the same or different agent or with a combination of agents. In some embodiments, the primary scaffold or the secondary scaffold or both may first be mixed with cells or a drug prior to producing the TI, and the combined components may be contacted to produce the final TI that comprises cells, drugs or a therapeutic agent.

In some examples, the tissue implant (TI) has the capacity for preloading of differentiated or undifferentiated cells to augment tissue repair. In the case of differentiated cells, chondrocytes, osteoblasts, tenocytes, fibroblasts, fibrochondrocytes and ligament cells can be isolated and applied by infusion, dropwise, wicking, pumping or injection, for healing of cartilage, bone, tendon, skin, meniscus or ligament, respectively, or for other tissue defects. In the case of undifferentiated cells, adult or immature mesenchymal cells derived from bone marrow aspirates, iliac crest needle biopsies or other dissociable mesenchymal tissues, such as somites, muscle, interstitial connective tissues, through enzymatic dissociation and subsequent culture, can be applied in methods similar or identical to differentiated cells. Other mature or immature undifferentiated cells may be from immortalized cell lines, hematopoietic stem cells, neural stem cells each having the capacity for differentiation in situ or may include embryonic stem cells which when isolated and placed within the localized defect can undergo differentiation to the target tissue. The number of cells to be applied may vary in accordance with the differentiated state of the cells and with their inherent proliferative capacity. The age of the cells may vary with origin and with time in culture.

In one embodiment, one of the scaffolds may be generated as a stand-alone structure. In this regard, a composition comprising a soluble collagen, alcohol treated derivatized collagen e.g., alcohol/salt treated methylated collagen or other alcohol/salt derivatized collagen, gelatin or methylated gelatin in an acidic solution further comprising a non-ionic surfactant can be subjected to neutralization, precipitation, dehydration, lyophilization and dehydrothermal treatment. A secondary scaffold as a stand-alone implant may be similarly loaded with cells and may optionally contain a pharmaceutical agent, growth modulator or another compound before or after implantation, as described above. The process for preparation of the stand-alone secondary scaffold can be modified to the extent that the composition for preparation of the secondary scaffold (basic solution) is placed into a container suitable to permit gelling, precipitation, dehydration, lyophilization and dehydrothermal treatment. The stand-alone secondary scaffold can be used for implantation in the same manner as described for the two scaffold TI. The treated, stand-alone secondary scaffold can be useful, for example, in the healing of tears in cartilage or skeletal tissues, such as, for example, the meniscus where it can be charged and/or supplemented with all of the tissue factors and cells, such as meniscal fibroblasts. The treated, stand-alone secondary scaffold can be used in a similar fashion for bone, tendon and ligament repair.

In some examples, the two-scaffold TI (primary and secondary scaffold) can provide distinctly improved properties when compared to the primary scaffold alone, to the secondary scaffold alone or to a composite loaded with a composition for preparation of the secondary scaffold, unprocessed, or to the composite that has been dehydrated and lyophilized. Typically, a tissue implant is implanted into a tissue defect during a surgery either already rehydrated (wet) or in a dry form. Also typically, such surgery has a time-limit on implantation that has about one hour window when the implant needs to be placed into the defect. For these reasons, it is important that a TI provide stability, resistance to change in shape, size and shrinkage or swelling, resistance to dissolution, consistency with respect to pore size permitting an ingrowth of cells into the implant and conditions for formation of extracellular matrix within the implant. The TI's described herein can provide such desirable attributes. A presence of the secondary scaffold improves the function of the TI by providing a multitude of small membranous substrates which can provide cell anchorage and phenotype stability while preserving the through porosity of the overall implant, thereby allowing nutrients and growth factors and migratory cells to permeate the implant. In the case of cartilage lesions, the migratory cells include chondrocytes from the debrided lesion which have been freed from damaged extra-cellular matrix through the up-regulation of certain matrix metalloproteinases.

Without wishing to be bound by any theory, implant stability may depend on several factors. There desirably is minimally low or almost no initial dissolution of collagen from the implant into the physiological fluids, and there desirably is minimally low or preferably no change in size and shape of the implant following rehydration or wetting before, during or after surgery prior to biodegradation in situ. The TI's described herein can include minimal initial collagen dissolution and minimal change in size and shape during the initial critical period. One of the desired attributes for the implant is its resistance to dissolution of its components upon wetting and rehydration of said implant during implantation during preparation of the TI for implantation and subsequently also after implantation. A minimally low dissolution or, preferably, almost no dissolution of the collagen component from the implant into the physiologic solution after or before placement of the implant into the tissue defect, and into an interstitial fluid, plasma or blood following the surgery, under normal physiological conditions ensures continued functionality of the implant following its implantation into the tissue defect, such as, for example into the cartilage lesion. Low or no dissolution of collagen from the implant means the high retention of the collagen within the implant.

Another desirable attribute of the TI is its resistance to change in size and shape. This feature is very important for implant efficacy as any change in the size and shape by shrinking or swelling can negatively affect the outcome of the implantation surgery. An implant that would get smaller by shrinking will not fill the defect, will not provide a structural support for migration of cells from the surrounding tissue or cell integration into the surrounding tissue and may also be dislodged from the defect. Swelling of the implant could, on the other hand, cause the implant to swell within the defect, decrease the structural support for cells and be rejected or ejected from the defect because of its larger size. The resistance to change in shape and size means that for implantation into a defect of discernable size, the functional construct must not swell or shrink extensively upon rehydration during time of preparation before surgery or after placement of the implant into the defect.

An additional desired attribute of the TI is to provide support and conditions for cell migration from surrounding tissue or for the cell integration into surrounding tissue in the case when the cells are seeded into the TI before implanting. This feature is determined by cell viability within the TI and provides another criteria for determining functionality and usefulness of the TI. In order for an implant to be functionally viable, the implant must provide a structural support for cells as well as provide or permit conditions to be provided for cell seeding into the implant, cell growth within the implant and/or cell migration into or from the surrounding tissue. Conditions for cell seeding, their growth within the implant, their nutritional and metabolic needs are designed based on the type of cells that the implant is supposed to deliver and support. For example, if the implant is designed for repair of a skin defect, the cells and their requirement will be different than if the implant is designed for repair of a chondral or bone lesion. Conditions for structural support and conditions for promotion of cell growth, their migration and/or integration into the surrounding tissue will be adjusted based on the tissue where the TI will be implanted and the function the implant will assume in repair of the tissue defect.

While the TI described herein is suitable for use in treatment and repair of chondral, subchondral or bone lesions, the TI is also suitable to be used for repair of any other tissue or tissue defect. The implant, such as, for example, wet or dry TI implanted into the cartilage lesion, desirably provides conditions allowing cells to form and generate a new extracellular matrix. In this regard, the implant porous structure must allow cells to migrate, be attached or aggregate into and within the pores and to function similarly to their normal function in the healthy tissue. The pore size of the implant and the consistency with respect to pore size for the ingrowth of cells is important both for cell adhesion, extracellular matrix production and cell to cell contact and communication. Depending on the tissue to be repaired, the pore size of the primary and/or secondary scaffold will vary. For example, cartilage scaffolds can comprise a pore size of approximately 200 microns and bone can comprise a pore size in the range of 300 to 350 microns. A significant attribute of having two scaffolds arises from the increase in mechanical integrity relative to a primary porous collagenous material because the polymerization can create fiber-like structure between the primary and secondary scaffold that serves as a reinforcing network for cells. In addition, due to inclusion of the secondary scaffold there is an increase in overall surface area within the TI that permits cells spreading and migration throughout the interstices of the TI. At the same time, the secondary scaffold can be designed such that it is not of such high density that it becomes a blocking agent that acts as a steric hindrance for cell ingrowth and tissue repair. The TI described herein can provide optimal conditions, such as implant stability, collagen retention, resistance to change in size and shape of the implant, pore size and surface area for viability and growth of cells within the implant.

One illustrative process for loading the secondary scaffold into the primary scaffold may comprise pre-loading, loading, polymerization, treatment of the TI, dehydrothermal treatment, packaging and surgical procedure. The pre-loading stage is a preparatory stage where the primary scaffold is either obtained from commercial sources or is prepared as described herein. A primary scaffold, typically a collagen or derivatized containing honeycomb, sponge or lattice providing a structural support for incorporation of the secondary scaffold is obtained. In one embodiment, a bovine Type I collagen matrix with honeycomb (HC) like structure is obtained, for example, from Koken, Inc. (Japan) or from other commercial sources and used as primary scaffold. However, such commercially available honeycomb matrices have typically randomly distributed pores of irregular shape and size. The pores of these structures are not always vertically positioned. In another embodiment, a primary honeycomb scaffold is produced, wherein said primary scaffold has randomly or non-randomly oriented pores of substantially the same size and shape. The shape and size of the primary scaffold can determine, at least in part, a size of the TI ultimately delivered to the surgeon for implantation into the tissue defect. Typically the TI has a rectangular, circular or oval shape with dimensions of about 50 mm and a vertical thickness of about 1 to 5 mm, preferable 1-2 mm. Illustrative dimensions of the TI for its preparation and, therefore, the dimensions of the primary scaffold are 50×50 mm×1.5 mm, with pores oriented substantially vertically, said pores having a pore size of from about 100 to about 400 microns, preferably about 200+/−100 microns and pore length of 1.5 mm. However, dimensions of the primary scaffold may be any that are required by the tissue defect to be repaired and that can be prepared by the process of the invention.

The next step in TI preparation comprises preparing a composition for preparation of a secondary scaffold. As noted herein, the secondary scaffold may be produced using one or more of the cohesive materials described herein. In other instances, a secondary scaffold may be produced by neutralization of a soluble collagen solution (or soluble alcohol, treated derivatized collagen solution as described herein) having an initial acidic pH of about pH 1.5-4, preferably between about pH 1.9-2.2, a collagen concentration from about 0.5 to about 10 mg/ml of collagen, preferably about 2.9 to about 3.2 mg/ml, and osmolality from about 20 to about 400 mOsm/kg, preferably about 28 to about 32 mOsm/kg. The soluble collagen solution (or soluble derivatized collagen solution) is then neutralized with any suitable base and/or buffer to pH in a range from about pH 7.3 to about pH 7.7 to derive a basic solution. Preferably, the solution is neutralized by adjusting pH to neutrality 7.4 using a collagen, 10× Dulbecco's phosphate buffered saline (DPBS) and 0.1 M NaOH in 8:1:1 ratio or using an aqueous solution or ammonia vapor in concentration sufficient to neutralize acid within the collagen solution. The final osmolality and pH of the basic solution is about 290 mOsm/kg and pH 7.4, respectively. As noted herein, the secondary scaffold may be prepared in the absence of a surfactant and/or in the presence of an alcohol or polyol or may comprise an alcohol/salt treated, derivatized collagen. The suitable buffers for solubilization of the Type I collagen are, for example, a formic acid containing buffer at pH 4.8, acetic acid containing buffer at pH 5.0 or a diluted hydrochloric acid containing buffer at pH 3.0. Neutralization is typically carried out using ammonia aqueous solution or a vapor of ammonia, or in concentration sufficient to neutralize the acidic pH over about 30 minutes to about 24 hours, preferably for 12 to 24 hours. This factor has also been found to affect the collagen polymerization and formation of pores having homogeneous pore size. However, other means of neutralization may also be conveniently used. The primary scaffold can then be loaded with a basic solution for the secondary scaffold comprising soluble collagen solution (or soluble derivatized collagen solution) and optionally one or more salts, alcohols or polyols. This basics solution is subsequently precipitated within pores of the primary scaffold. Loading the primary scaffold with the basic solution for the secondary scaffold is performed using any suitable method. Soaking, wicking, submerging the primary scaffold in the solution, electrophoresis and any other suitable means. Once the basic solution for the secondary scaffold is introduced into the primary scaffold, a composite of both is subjected to a process or treatment that results in formation of the secondary scaffold inside pores of the primary scaffold. The neutralized basic solution can be loaded into the primary scaffold by placing from about 3.75 to about 7.5 ml (approximately 1 to 2× volume), preferably a volume about 4.9 ml (approx. 1.3× volume of the primary scaffold) of the secondary scaffold basic solution on the bottom of a dish and then placing the primary scaffold in this solution and allowing it to be soaked up.

In some examples, the primary scaffold loaded with the neutralized basic solution comprising the soluble collagen is then subjected to conditions resulting in precipitation of the neutralized basic solution within the pores of the primary scaffold thereby generating a structurally distinct secondary scaffold. Typically, and allowing for variability of the basic solution or composition used for creating of the secondary scaffold, the composition introduced into the pores of the primary scaffold is gelled or precipitated within said primary scaffold and may also be cross-linked using chemicals such as glutaraldehyde or another multifunctional aldehyde, where the aldehyde reacts with amino groups of the collagen yielding a Schiff base, which can be stabilized by a reduction reaction; carbodiimide reagent, such as carbodiimide 1-ethyl-3-(3-dimethyl aminopropyl)-carbodiimide (EDC)

with or without N-hydroxy-succinimide (NHS) where the NHS is used to suppress side reactions. Additionally, EDC and NHS can be used in combination with diamine or diacid compounds to introduce extended cross-links; acyl azide where the acid are activated and subsequently reacted with an adjacent amine group; epoxy compounds such as 1,4-butanediol diglycidyl ether, or cyanamide. In some instances, the NHS based reactant may be monofunctional, difunctional or multifunctional.

In addition, irradiation such as short wave length UV irradiation (254 nm) can introduce cross-links in the collagen. The primary scaffold can be loaded with the solution that forms the secondary scaffold in a range from about 1 to about 2 volumes of the primary scaffold is then placed in an incubator at a temperature from about 25 degrees Celsius to about 38 degrees. Celsius, preferably to about 37 degrees Celsius. temperature, typically for from about 10 minutes to about 18 hours, more typically for about 20 to about 100 minutes, preferably for about 40 to 60 minutes, and most preferably for a time when the precipitation of the collagen solution, e.g., derivatized collagen solution, into a solid secondary scaffold occurs.

In order to assure that the vast majority of the salt of the precipitated collagen solution within the pores of the primary scaffold is removed, a composite consisting of the primary scaffold having the secondary scaffold precipitated within can be subjected to one or more washing steps whereby the majority of the salts are removed. The composite comprising the primary scaffold and the secondary scaffold precipitated within, can be washed by placing said composite in a volume of from about 20 mL to about 10 liters, preferably about 500 mL, of de-ionized water further containing one or more buffers and/or a non-ionic surfactant. The surfactant is typically present in concentration from about 0.05 to about 1.0 mg/ml, preferably about 0.23 mg/ml. Where a surfactant is used in the washing process, one or more final washing steps using a solution that is surfactant free may be performed to ensure no surfactant remains behind. In other instances, the entire construct can be washed without using any surfactants.

Typically, the washing step takes approximately 15-30 minutes. There may be one or several washing step repetitions. All excess non-precipitated collagen is removed during the extraction from the composite into the wash solution. Polymerizing of the collagen present in the secondary scaffold solution loaded within the primary scaffold pores results in formation of a stable composite TI comprising the primary scaffold and the secondary scaffold precipitated therein.

In some instances, following the precipitation or gelling and washing, the composite can be subjected to lyophilization and dehydrothermal treatment. In some instances, alcohol/salt of the entire composite structure can be performed prior to lyphophilization, whereas in other instances, alcohol/salt treatment of the entire composite can be performed after lyophilization but before dehydrothermal treatment. In other instances, alcohol/salt treatment of the entire composite can be performed after dehydrothermal treatment. As noted herein, treatment with alcohol/salt may increase the stickiness, e.g., increase the stickiness of the entire composite. Where suitable stickiness is achieved, the TI can be implanted without the use of any adhesive or material to hold the TI at the defect site.

The solid composite can then be dehydrated using any method suitable for such dehydration. Typically, such dehydration will be freeze-drying or lyophilization. Freezing is typically carried out at temperature from about −10 degrees Celsius to about −210 degrees Celsius, preferably from about −80 degrees Celsius, over a period of about 2 to about 60 minutes. The frozen composite is then lyophilized forming a lyophilized composite. The gradual nature of the polymerization and slow process of water removal typically maintains the architectural elements of the secondary scaffold and achieves the proper orientation and diameter of the pores.

The frozen and dehydrated solid TI is then subjected to lyophilization. The frozen dehydrated composite is removed from the freezer and placed into a pre-cooled lyophilization chamber. Lyophilization typically occurs in about 15-21 hours, depending on the size and shape of the composite but is typically and preferably completed in about 18 hours.

To further stabilize the composite and to achieve necessary stability, resistance to dissolution and sterility of the final product, the solid TI can be subjected to dehydrothermal (DHT) treatment. DHT treatment achieves cross-linking of the collagen and at higher temperatures can also sterilize the TI. This cross-linking step can prevent dissolution of the secondary scaffold upon rehydration before or after implantation. In other instances, DHT may be omitted to keep the TI sticky prior to implantation.

The lyophilized, TI can be placed into a dry glass chamber or container and covered with the glass, aluminum foil or another suitable material resistant to higher temperatures. The container with the lyophilized TI can be placed into the pre-heated dehydrothermal oven and subjected to a temperature in a range from about 70 degrees Celsius to about 200 degrees Celsius, under vacuum, for about 30 minutes to about 7 days, preferably for about 5-7 hours and most preferably for about 6 hours. As noted herein such treatment stabilizes the composite, makes it resistant to collagen dissolution upon wetting, provides for rapid wetting and assures none or minimal shrinkage or swelling upon wetting with a physiological solution or buffer, and sterilizes the double-structured tissue implant.

The TI fabricated by the process described above is then ready for a sterile packaging and storage. In this form, the TI should have a long shelf-life. The TI can be removed from the dehydrothermal oven and transferred aseptically into sterile environment, such as a Bio Safety Cabinet (BSC), where it is packaged under conditions assuring sterility. The TI is then ready to be stored at room temperature until its use. Packaged TI can be delivered or made available to a surgeon for implantation into a tissue defect.

During surgery, a surgeon determines an extent of the defect or lesion to be repaired, opens the packaged product, cuts the TI to the size of the defects and places the cut-to-size piece into said defect. The TI may be wetted before the implantation and then placed into the defect or alternatively, it may be placed into the defect in a dry form and a suitable physiologically acceptable solution may be then added to wet the implant in situ. In other instances, the TI may be exposed to an alcohol/salt solution immediately prior to use to increase its stickiness prior to implantation. For example, a first syringe may comprise an alcohol/salt solution that is then mixed with the TI prior to implantation. The treated TI may then be implanted into the defect site with or without an adhesive layer.

Since the implant is very stable, and does not change its size or shape significantly by shrinking or swelling, the implant fits tightly into the defect or lesion. To assure that the implant stays within the defect or lesion, such defect or lesion can be first coated with a suitable tissue adhesive, sealant or glue that keeps the implant in place. In some instances, the TI may first be coated with one of the cohesive materials described herein optionally in combination with an adhesive, sealant or glue. In an alternative illustration, the defect or lesion may be pretreated with microfracture where the tissue underlying the lesion or defect is microfractured with microchannels to permit the blood and nutrient supply into the lesion or defect, lining the defect or lesion but not the microfracture, with the adhesive, glue or sealant and placing the implant as described above. In both instances, the implant placed into the lesion or defect may optionally be covered with another layer of the adhesive, sealant or glue or may be covered with a layer of treated, cohesive material as described herein. In some instances, cells, drugs or modulators may be loaded into the TI attached to the second scaffold before implantation and wetting, during wetting following the implantation, or independently provided after the implantation.

In some instances, two methods suitable for implantation of a TI into the tissue defect or lesion can be used. The first method comprises implantation of the TI into the lesion without any special pretreatment of the lesion other than debriding and removing any undesirable debris from the defect or lesion before the TI implantation. The second method comprises pretreatment of the defect or lesion with a microfracture technique. In such a case, a subchondral plate of the lesion is penetrated with microchannels connecting the bottom of the lesion or defect with underlying bone to permit the migration of cells, blood and nutrients into the deposited TI within the lesion or defect.

Additionally, the implantation method comprises, for example, two variations in attaching and sealing the TI within the defect or lesion. In the first mode, the TI is placed into the defect site and the tissue adhesive (or one or more of the cohesive materials described herein) is placed over the defect containing the TI. The second variation of the implantation method comprises, additionally, a step of placing a second adhesive (or one or more of the cohesive materials described herein) at the bottom of the lesion or defect before the placement of the TI. For example, when the TI is prepared as an implant seeded with in vitro cultured and/or activated cells when the implant itself is already filled with cells and extracellular matrix, rather than being rehydrated with solution of cells or bone marrow, the deposition of the bottom adhesive may be desired. Adhesives suitable for sealing the defect and securing it may be the same or different and are, typically, compounds polymerizable within short time from about 30 seconds to about 4 minutes with or without use of a curing means are well known. The cells that may be seeded into the TI in vitro may be cultured and activated using an intermittent hydrostatic pressure, as described in U.S. patent application Ser. Nos. 10/626,459, 10/104,677, 10/625,822, 10/625,245 and 10/882,581, each of which is hereby incorporated by reference in their entirety. Intermittently applied hydrostatic pressure has been shown to support development of a new hyaline cartilage in articular joints. In some instances, the tissue sealant or adhesive useful for the purposes of this application has adhesive, or peel strengths at least 10 N/m and preferably 100 N/cm; has tensile strength in the range of 0.2 MPa to 3 MPa, but preferably 0.8 to 1.0 MPa. Other adhesives can also be used including, for example, gelatin and di-aldehyde starch described in PCT WO 97/29715, 4-armed pentaerythritol tetra-thiol and polyethylene glycol diacrylate described in PCT WO 00/44808, photo-polymerizable polyethylene glycol-co-poly(a-hydroxy acid) diacrylate macromers described in U.S. Pat. No. 5,410,016, periodate-oxidized gelatin described in U.S. Pat. No. 5,618,551, serum albumin and di-functional polyethylene glycol derivatized with maleimidyl, succinimidyl, phthalimidyl and related active groups described in PCT WO 96/03159. Additional sealants and adhesives include sealants prepared from gelatin and dialdehyde starch triggered by mixing aqueous solutions of gelatin and dialdehyde starch which spontaneously react and/or those made from a copolymer of polyethylene glycol and polylactide, polyglycolide, polyhydroxybutyrates or polymers of aromatic organic amino acids and sometimes further containing acrylate side chains, gelled by light, in the presence of some activating molecules. Another type of the suitable sealant is 4-armed polyethylene glycol derivatized with succinimidyl ester and thiol plus methylated collagen in two-part polymer compositions that rapidly form a matrix where at least one of the compounds is polymeric, such as polyamino acid, polysaccharide, polyalkylene oxide or polyethylene glycol and two parts are linked through a covalent bond, for example a cross-linked derivatized PEG with methylated collagen, such as methylated collagen polyethylene glycol. In some instances, illustrative sealants are 4-armed tetra-succinimidyl ester PEG, tetra-thiol derivatized PEG and PEG derivatized with methylated collagen (known as CT3), commercially available from Cohesion Inc., Palo Alto, Calif. and described in U.S. Pat. Nos. 6,312,725B1 and 6,624,245B2 and in J. Biomed. Mater. Res., 58:545-555 (2001), J. Biomed. Mater. Res., 58:308-312 (2001) and The American Surgeon, 68:553-562 (2002), all hereby incorporated by reference. Sealants and adhesives described in U.S. patent application Ser. No. 10/921,389 filed Aug. 18, 2004 and 11/525,782 filed Dec. 22, 2006 may also be used.

In certain configurations, cells may be activated prior to or after loading into the TI. For example, cells can be isolated, seeded into the TI and then subject to a static, constant or cyclic hydrostatic pressure above atmospheric pressure (about 0.5-3.0 MPa at 0.5 Hz) with medium perfusion rate for several (5-10) days, and then a resting period of ten to fourteen days at constant (atmospheric) pressure. A combination of hydrostatic pressure and static pressure can have advantage over conventional culture methods by resulting in higher cell proliferation and extracellular matrix accumulation within the TI. Use of the TI maintains uniform cell distribution within the primary and secondary scaffolds that also provides support for newly synthesized extracellular matrix. Obtained seeded TI is easy to handle and manipulate and can be easily stored and safely implanted in a surgical setting. Increased cell proliferation shows that the harvested inactive non-dividing cells, particularly chondrocytes, have been activated into active, dividing and multiplying chondrocytes. Increased level of DNA shows genetic activation of inactive chondrocytes. Increased production of Type II collagen and S-GAG shows that production of the extracellular matrix has been activated using the method for activation described above. It is to be understood that these conditions may be advantageously changed using variations of ranges of cyclic hydrostatic pressure, flow rate, duration of the pressure and resting period, particularly when applied to different cells or tissue. All variations of all conditions and combinations thereof are intended to be within the scope of this invention.

To be successful for treatment of articular cartilage, the TI desirably provides conditions allowing the chondrocytes or mesenchymal stem cells seeded therein to be able to form, generate or induce the generation of the new extracellular matrix. In this regard, the TI pore structure desirably permits cells to migrate into the pores and function similarly to their normal function in the healthy tissue. The extracellular matrix formed by the cells seeded within the TI then provides means for growing a new hyaline or hyaline-like cartilage for treatment, replacement or regeneration of the damaged or injured articular cartilage. Such treatment is currently difficult because of the unique properties of the articular cartilage that is not the same as and does not behave as other soft tissues.

In addition to cartilage repair, a number of other chronic conditions represent instances where the implantation of the double structured scaffold can provide a clinically important bridge for tissue repair. For example, genitourinary tissues have been fabricated from a variety of materials. The TI once placed at the site of tissue damage will provide a support for development of new tissues occurs in accordance with predefined configuration. In these applications, similar to cartilage, the TI must resist the dynamic forces generated by the surrounding muscle and connective tissues and maintaining its structure during a necessary period of cellular infiltration and tissue formation. The rapidity by which tissue differentiation and structural integrity are established is subject to modulation through the use specific signaling factors localized within the primary and secondary collagenous composite. Although the limits by which, for example, new muscle formation can be derived from progenitor cells, suggests that localization of the mesenchymal cells to the site of damage in response to homing molecules, such as chemokines and cell receptor ligands, may be used to accelerate repair of muscle, either cardiac or skeletal. The TI may be used to deliver these cells or modulators to the site of damage. Finally, wound healing applications have remained a primary goal in the use of tissue implants for cell-based tissue repair. Treatment of acute and chronic wounds is dependent on a multi-faceted transition by which progenitor cells encounter soluble mediators, formed blood elements, extracellular matrix macromolecules and parenchymal cells that then serve to reestablish a body surface barrier through epithelialization. In this instance either the TI or the stand alone secondary scaffold implant may provide a novice stromal layer into which blood vessels and progenitor cells can migrate. From this migration, the progenitor cells may then undergo differentiation into the fibroblast stromal cell and generate or recruit epithelial cells to support reestablishment of dermal and epidermal layers at the time of wound closure.

In certain embodiments, the TI and/or the primary or secondary scaffolds used in the TI can be used in one or more layers of a bilayer. In some instances, the bilayer may comprise two or more different cohesives. In other configurations, one cohesive material is present in a first layer, and a treated scaffold (primary or secondary) or TI is then disposed on the cohesive material as the second layer of the bilayer. One or both layers of the bilayer may be loaded with a therapeutic or biologically active molecule. For example, a cohesive material comprising alcohol/salt treated, methylated collagen (or alcohol/salt treated, alkylated collagen) can be loaded with demineralized bone powder (treated to retain the BMP's) and used as a layer facing the osteoarthritic bone. A treated scaffold (primary or secondary) or TI may be disposed on the cohesive material layer to heal cartilage and may comprise bone marrow aspirate or centrifuged aspirate or pluripotent cells from the patient's fatty tissue. This bilayer can be used, for example, to treat sport induced osteochondral lesions. The bi-layered scaffold covers a large area and the layer facing the bone, as it regels, slowly releases the BMP's to stimulate new bone production. The treated scaffold or TI layer may include pluripotent cells and can be used, for example, for the cartilage repair.

Certain specific examples are described below to illustrate further some of the novel aspects of the technology described herein.

EXAMPLE 1

An alkylated collagen is dehydrated, preferably by lyophilization. A 50:50 solution of 100% Ethanol and 20×PBS is prepared and the alkylated collagen is dissolved therein. The concentration of alkylated collagen may be in the range of 10-1000 mg/ml. After collagen is dissolved, a volume of 100% ethanol equal to that of the 50:50 solution of 100% Ethanol and 20×PBS is added. As result of the additional addition of ethanol the collagen will form a precipitate. The collagen precipitate exhibits adhesive properties which are enhanced by pressure, i.e. it behaves like a pressure sensitive adhesive.

EXAMPLE 2

Two different types of collagen were tested using the protocol of Example 1—a bovine atelocollagen derived from skin and a methylated collagen derived from the same source. When the cohesive materials were placed between the palmar surface of the distal phalanx of the thumb and index finger, there was resistance to separation. Separating the thumb and index finger drew out the derivatized collagen in long fibrous strands for about 25 mm prior to breaking.

Potential uses are a putty in a tissue defects such as cartilage and/or bone defects. In the case of a bone defect, the adherent collagen may be mixed with a calcium source such as a calcium salt, hydroxyapatite powder, or demineralized bone powder and used as a bone filler, for example,

EXAMPLE 3

Figure 2A:
FIGS. 2A-2D are photographs showing a cohesive material disposed in a defect in a cow femur, in accordance with certain examples.
Figure 2B:
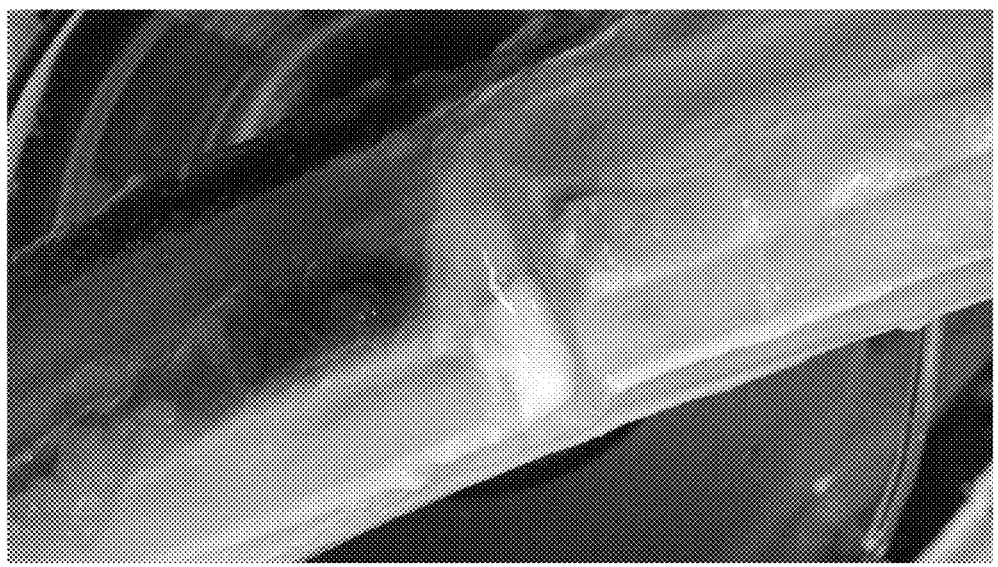
Figure 2C:
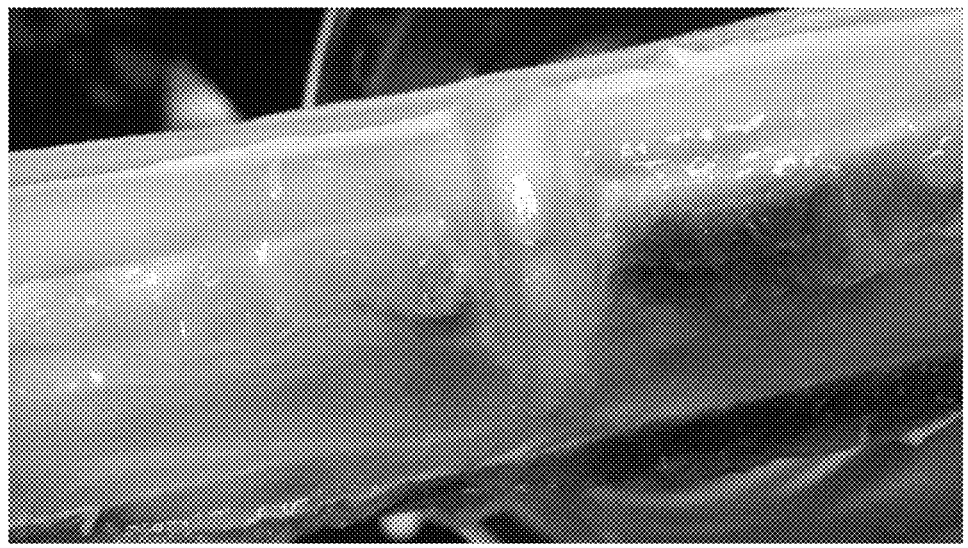
Figure 2D:

A bone defect was produced in a cow femur using a hacksaw. The material produced in Example 1 was added to the defect. The ability of the added material to be retained under the force of gravity was monitored over time at 37 degrees Celsius at 0 minutes (FIG. 2A), 10 minutes (FIG. 2B), 20 minutes (FIG. 2C) and 35 minutes (FIG. 2D). The material was retained within the defect over the 35 minute test window.

EXAMPLE 4

Figure 3:
FIG. 3 is a photograph showing a cohesive material disposed in a defect of a chicken bone, in accordance with certain examples.

A bone defect was produced in a chicken bone. The material produced in Example 1 was added to the defect. After 20 hours, the material remained stuck to the defect site (see FIG. 3).

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method of producing a cohesive material comprising:
   alkylating an atelopeptide collagen with an alkylating group to provide an alkylated atelopeptide collagen;
   adding the alkylated atelopeptide collagen to a solution comprising alcohol and salt to solubilize the alkylated atelopeptide collagen; and
   after the alkylated atelopeptide collagen is solubilized using the solution comprising the alcohol and the salt, adding additional alcohol to the solution comprising the solubilized, alkylated atelopeptide collagen to increase stickiness of the solubilized, alkylated atelopeptide collagen and provide treated atelopeptide collagen; and
   separating the treated atelopeptide collagen from the solution and the additional alcohol to provide the cohesive material.

2. The method of claim 1, further comprising separating the treated atelopeptide collagen by evaporating the solution and the additional alcohol.

3. The method of claim 1, further comprising selecting the alkylating group to comprise one to three carbon atoms.

4. The method of claim 1, further comprising mixing the cohesive material with at least one pharmaceutically active compound.

5. The method of claim 1, further comprising conjugating the alkylated atelopeptide collagen to at least one pharmaceutically active compound prior to adding the alkylated atelopeptide collagen to the solution comprising the alcohol and the salt.

6. The method of claim 1, further comprising producing the cohesive material without the use of a surfactant.

7. The method of claim 1, further comprising electrospinning the cohesive material.

8. The method of claim 1, further comprising lyophilizing the solution comprising the cohesive material.

9. The method of claim 1, further comprising applying a pressure to the cohesive material to increase its adherence.

10. The method of claim 1, further comprising adding a second alkylated collagen, different from the alkylated atelopeptide collagen, to the solution comprising the alcohol and the salt prior to adding the additional-alcohol.

* * * * *